United States Patent [19]

McGarry et al.

[11] Patent Number: 5,366,479
[45] Date of Patent: Nov. 22, 1994

[54] SURGICAL STAPLE FOR ATTACHING AN OBJECT TO BODY TISSUE

[75] Inventors: Richard A. McGarry, Norwalk; David T. Green, Westport; Henry Bolanos, East Norwalk, all of Conn.; Wayne P. Young, Brewster, N.Y.

[73] Assignee: United States Surgical Corporation, Norwalk, Conn.

[21] Appl. No.: 100,613

[22] Filed: Jul. 30, 1993

Related U.S. Application Data

[62] Division of Ser. No. 782,290, Oct. 18, 1991, Pat. No. 5,289,964.

[51] Int. Cl.⁵ .............................. A61B 17/00
[52] U.S. Cl. ........................ 606/219; 606/151; 227/902
[58] Field of Search ............ 606/75, 151, 213, 219; 227/902

[56] References Cited

U.S. PATENT DOCUMENTS

| | | |
|---|---|---|
| 389,660 | 9/1888 | Mandel et al. |
| 3,054,406 | 9/1962 | Usher . |
| 4,014,492 | 3/1977 | Rothfuss . |
| 4,043,504 | 8/1977 | Hueil et al. |
| 4,127,227 | 11/1978 | Green . |
| 4,196,836 | 4/1980 | Becht . |
| 4,256,251 | 3/1981 | Moshofsky . |
| 4,261,244 | 4/1981 | Becht et al. |
| 4,321,002 | 3/1982 | Froehlich . |
| 4,347,847 | 9/1982 | Usher . |
| 4,375,866 | 3/1983 | Giersch et al. |
| 4,399,810 | 8/1983 | Samuels et al. |
| 4,403,693 | 9/1983 | Froehlich . |
| 4,407,286 | 10/1983 | Noiles et al. |
| 4,452,245 | 6/1984 | Usher . |
| 4,454,875 | 6/1984 | Pratt et al. ............ 606/219 |
| 4,470,532 | 9/1984 | Froehlich . |
| 4,485,816 | 12/1984 | Krumme . |
| 4,489,875 | 12/1984 | Crawford et al. |
| 4,505,273 | 3/1985 | Braun et al. |
| 4,519,532 | 5/1985 | Foslien . |
| 4,523,695 | 6/1985 | Braun et al. |
| 4,523,707 | 6/1985 | Blake, III et al. |
| 4,526,174 | 7/1985 | Froehlich ............ 606/219 |
| 4,532,927 | 8/1985 | Miksza, Jr. . |

(List continued on next page.)

FOREIGN PATENT DOCUMENTS

| | | |
|---|---|---|
| 1164133 | 10/1958 | France . |
| 1169438 | 12/1958 | France . |
| 2703529 | 8/1978 | Germany . |

OTHER PUBLICATIONS

U.S. Patent Appln. Ser. No. 08/035,512, filed Mar. 22, 1993, which is a file wrapper continuation of U.S. Patent Appln. Ser. No. 07/631,373, filed Dec. 20, 1990.

(List continued on next page.)

*Primary Examiner*—Stephen C. Pellegrino
*Assistant Examiner*—Jeffrey A. Schmidt

[57] ABSTRACT

An apparatus and surgical staple are disclosed for endoscope application of the surgical staples for attaching surgical mesh to body tissue in laparoscopic hernia surgery. The surgical staple is formed of a length of wire having a central portion having a middle portion and end portions extending therefrom in a first direction. Wire leg members extend in a direction generally perpendicular to the middle portion. Bridge portions are provided to connect each leg member to the end portions of the central portion. The bridge portions each have a straight portion substantially parallel to the middle portion and extending away from the end portions of the central portion. A first generally arcuate portion connected to the straight portions has a concave surface portion facing in a direction generally inwardly toward the opposing leg member. The first generally arcuate portions are connected to the leg members and at least a portion of each arcuate portion extends from the straight portions and generally in the first direction. A second arcuate portion on the leg members connects the leg member to the first arcuate portion. The free ends of the leg members are sharp to penetrate the body tissue in a manner to attach the portion of the mesh to the body tissue.

5 Claims, 14 Drawing Sheets

U.S. PATENT DOCUMENTS

| | | |
|---|---|---|
| 4,592,498 | 6/1986 | Braun et al. . |
| 4,607,638 | 8/1986 | Crainich ............................ 606/219 |
| 4,610,251 | 9/1986 | Kumar . |
| 4,655,221 | 4/1987 | Devereux . |
| 4,662,555 | 5/1987 | Thornton . |
| 4,664,305 | 5/1987 | Blake, III et al. . |
| 4,671,279 | 6/1987 | Hill . |
| 4,719,917 | 1/1988 | Barrows et al. . |
| 4,747,531 | 5/1988 | Brinkerhoff et al. . |
| 4,787,387 | 11/1988 | Burbank, III et al. . |
| 4,802,478 | 2/1989 | Powell . |
| 4,807,628 | 2/1989 | Peters et al. . |
| 4,821,939 | 4/1989 | Green . |
| 4,821,942 | 4/1989 | Richards et al. . |
| 4,838,884 | 6/1989 | Dumican et al. . |
| 4,874,122 | 10/1989 | Froelich et al. . |
| 4,887,601 | 12/1989 | Richards ............................ 606/219 |
| 4,899,745 | 2/1990 | Laboureau et al. . |
| 4,919,152 | 4/1990 | Ger . |
| 4,919,320 | 4/1990 | Storace . |
| 4,944,443 | 7/1990 | Oddsen et al. . |
| 5,053,038 | 10/1991 | Sheehan ............................ 606/75 |
| 5,125,553 | 6/1992 | Oddsen et al. . |
| 5,161,725 | 11/1992 | Murray et al. . |
| 5,174,487 | 12/1992 | Rothfuss et al. . |
| 5,222,975 | 6/1993 | Crainich . |
| 5,246,156 | 9/1993 | Rothfuss et al. . |

OTHER PUBLICATIONS

U.S. Patent Appln. Ser. No. 08/073,632, filed Jun. 8, 1993, which is a file wrapper continuation of U.S. Patent Appln. Ser. No. 07/686,795, filed Apr. 17, 1991.

M-D-D-I Report, Sep. 1991, Ethicon Endoscopic Staple for Hernia Repair.

Publication Entitled "A Quick Stapler Tie-Over Fixation For Skin Grafts", by Haim Y. Kaplan, M.D., Ann. Plast. Surg., 22:173, 1989, pp. 173–174.

Publication Entitled "A Rapid and Effective Method of Skin Graft Stabilization In Burned Children", by J. B. Boyd et al., The Hospital For Sick Children, Toronto, Canada, 1982, pp. 400–401.

Publication Entitled "A Simple Bolster Technique For Skin Grafting", by Henry T. Hoffman, M.D. and Michael LaRouere, M.D., Department of Otolaryngology, University of Michigan, Laryngoscope 99, May 1989, p. 5.

Information Booklet for Auto Suture® Skin & Fascia Suture® Surgical Stapling Instruments.

Information Booklet for Auto Suture® Multifire Premium ™ Disposable Skin Stapler and Disposable Loading Unit.

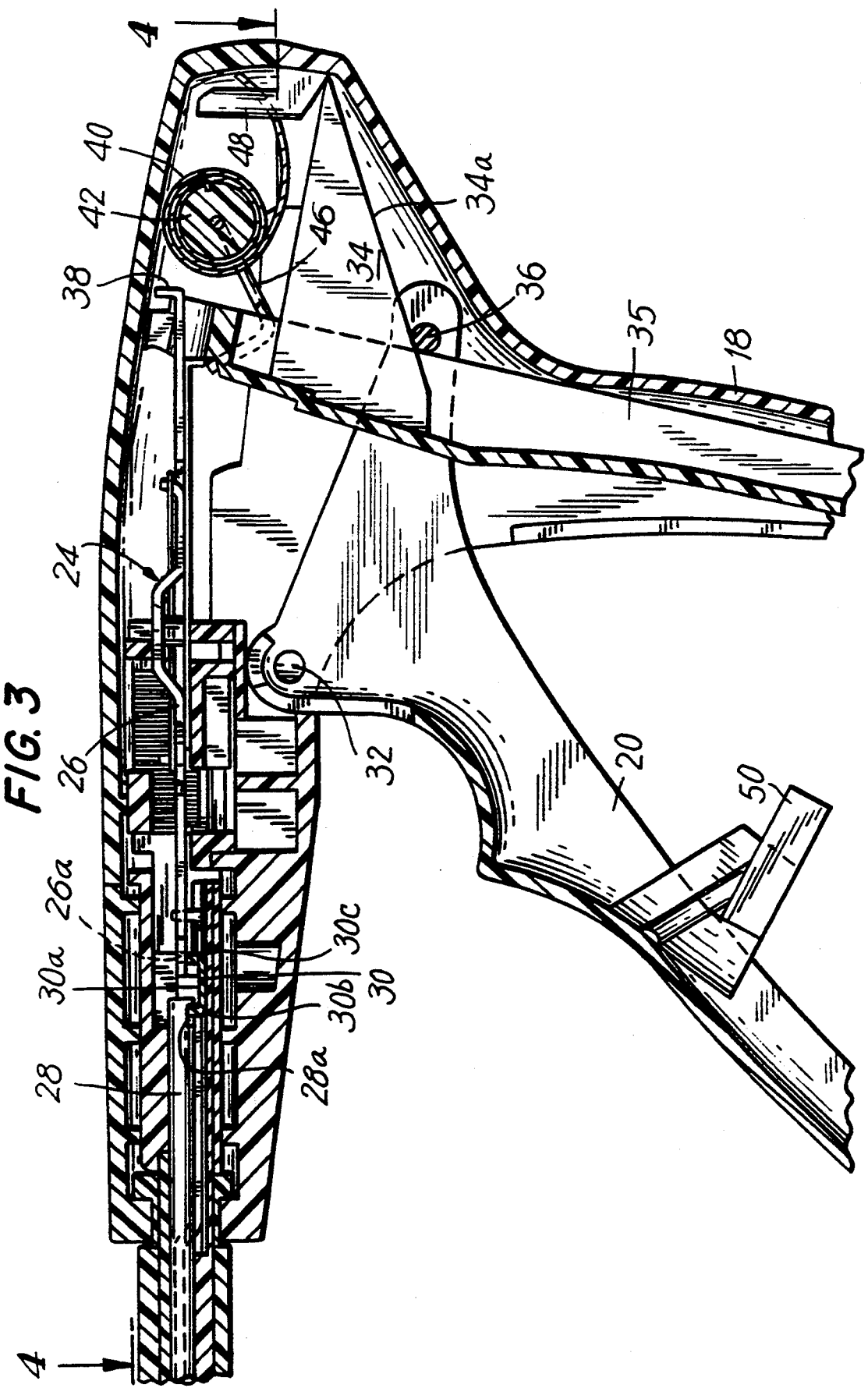

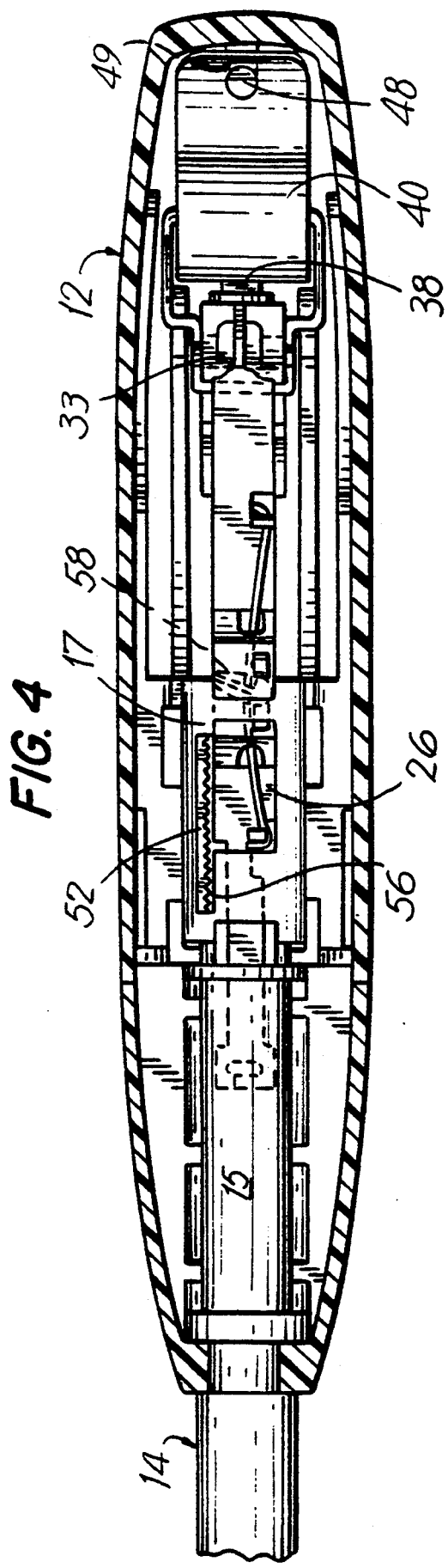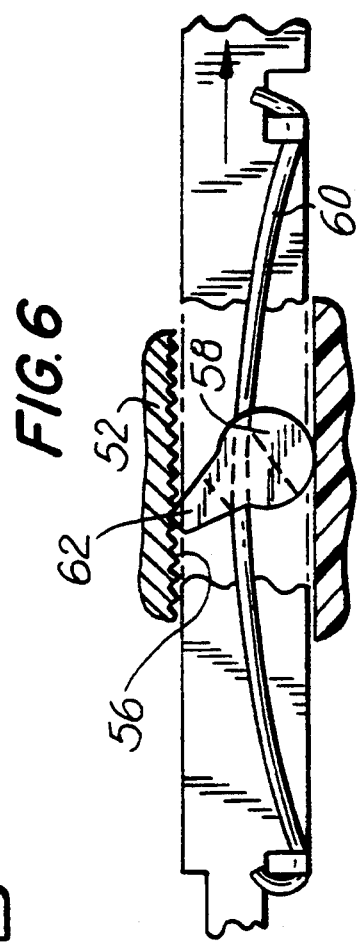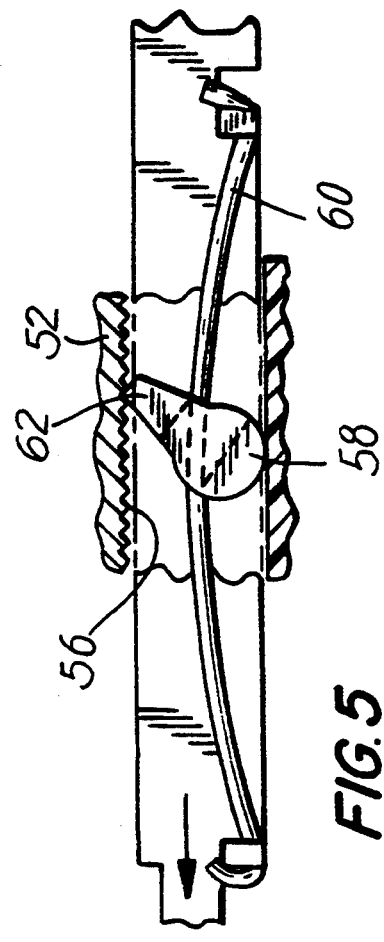

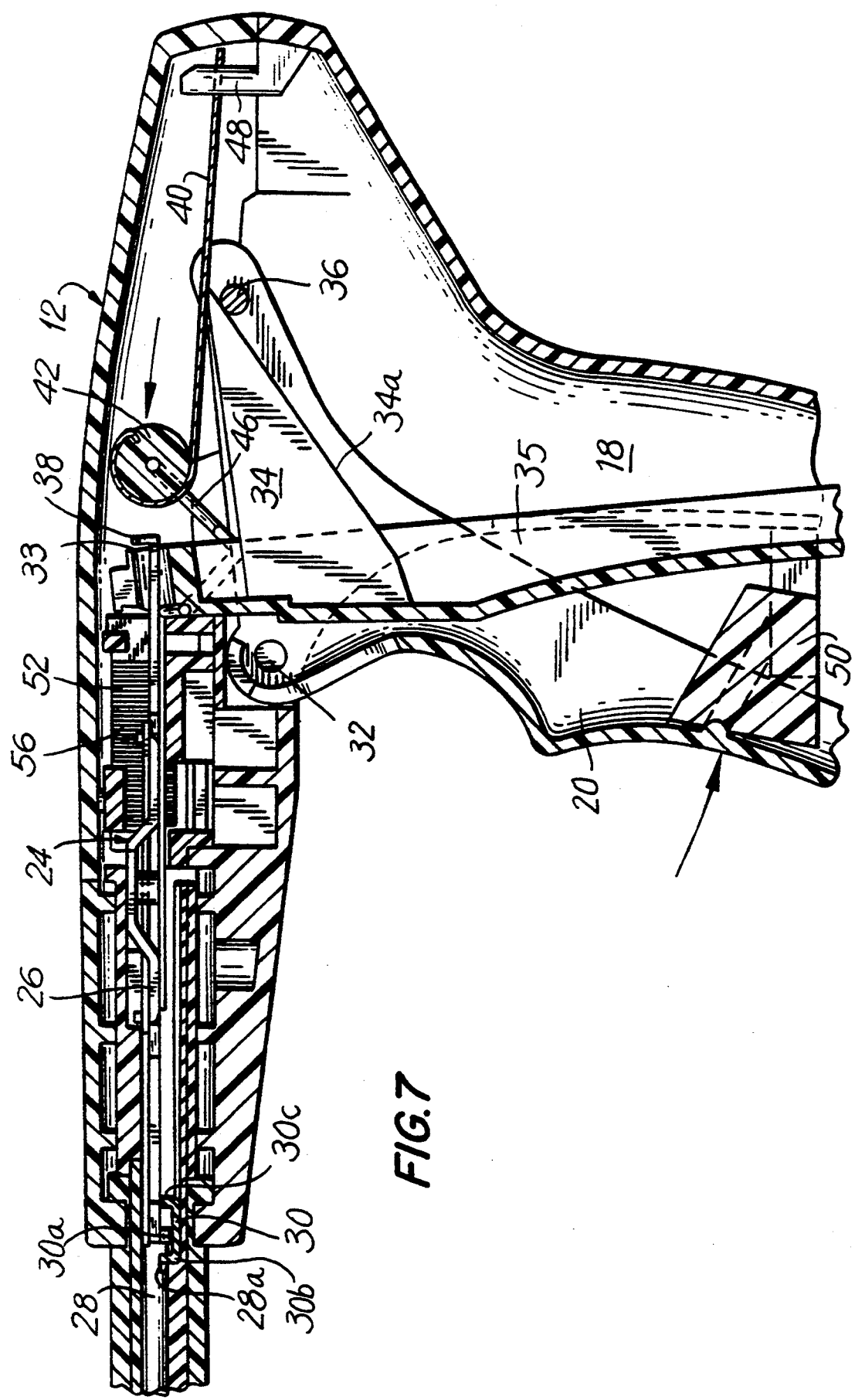

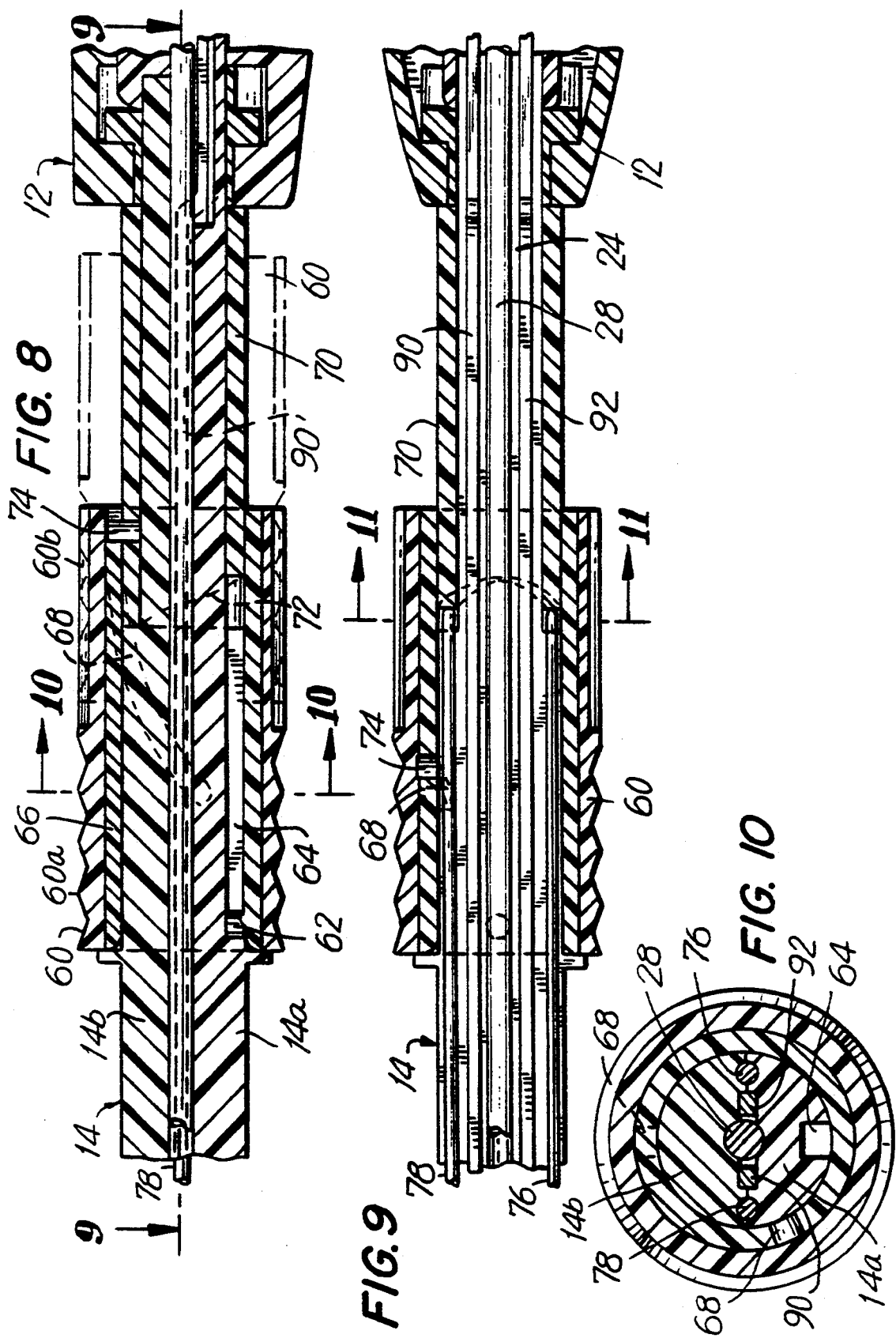

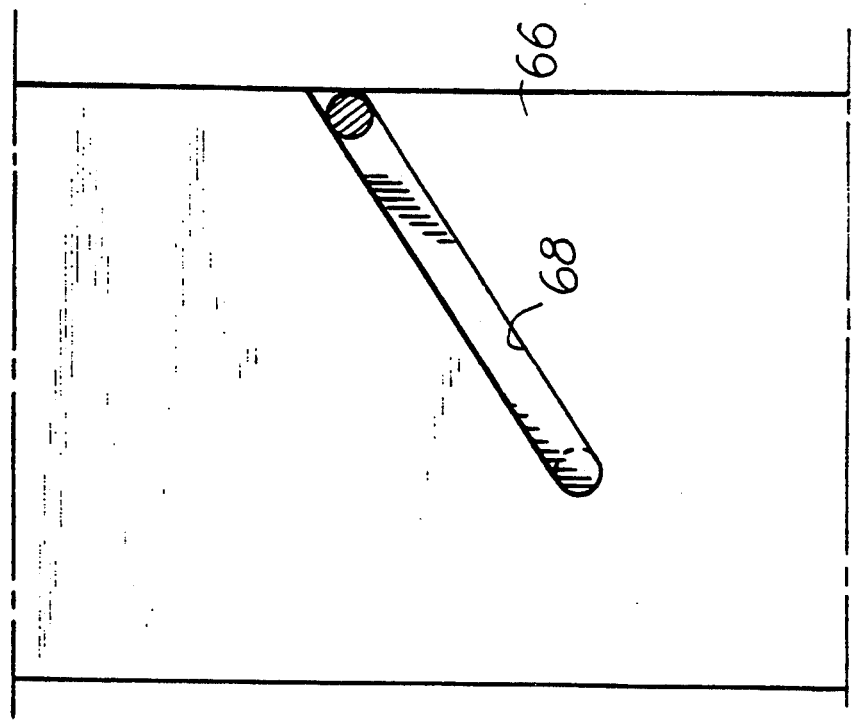
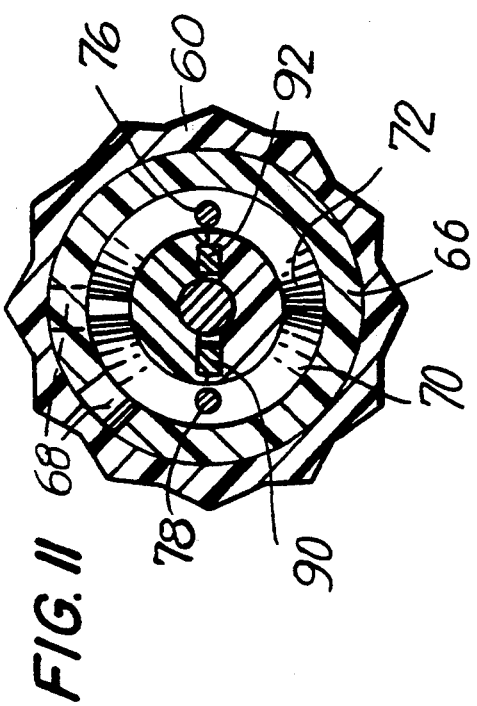
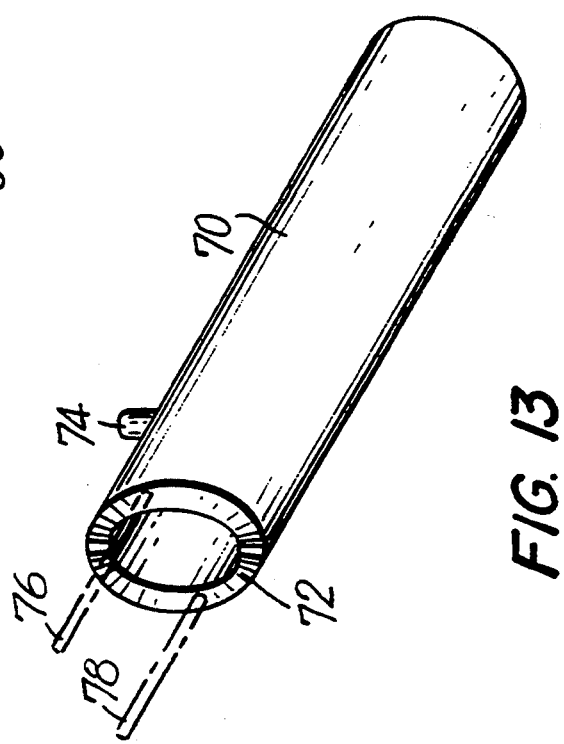

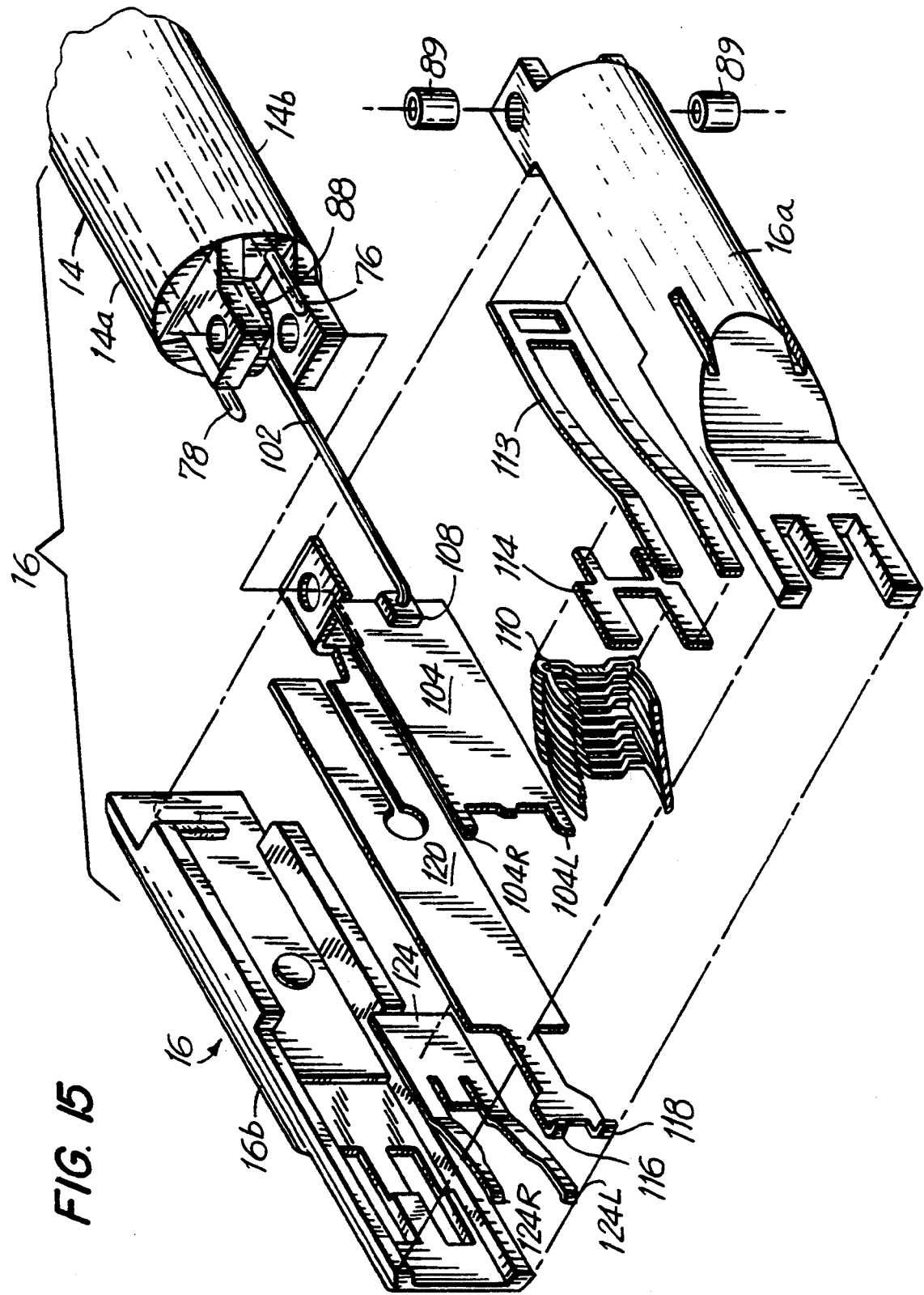

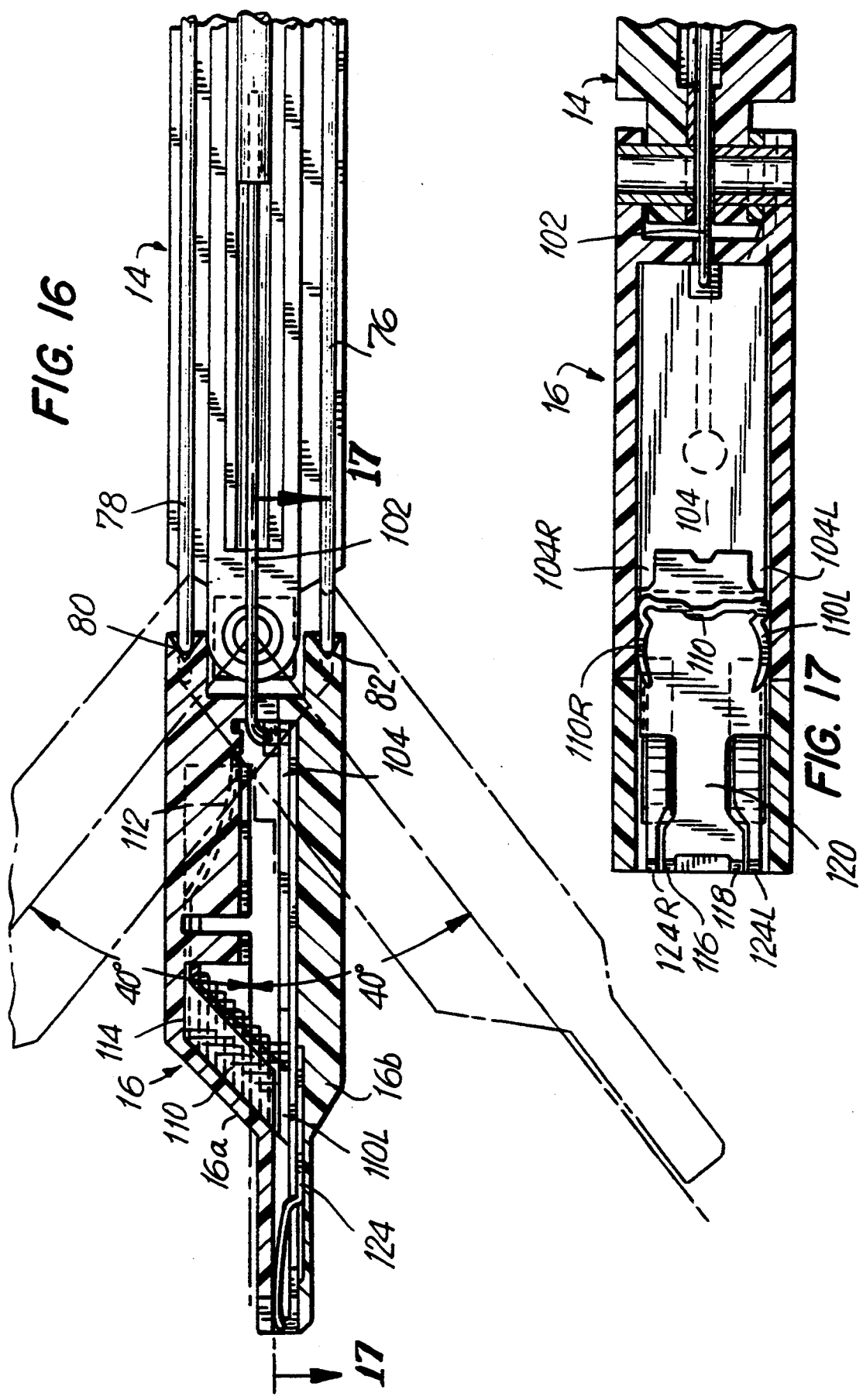

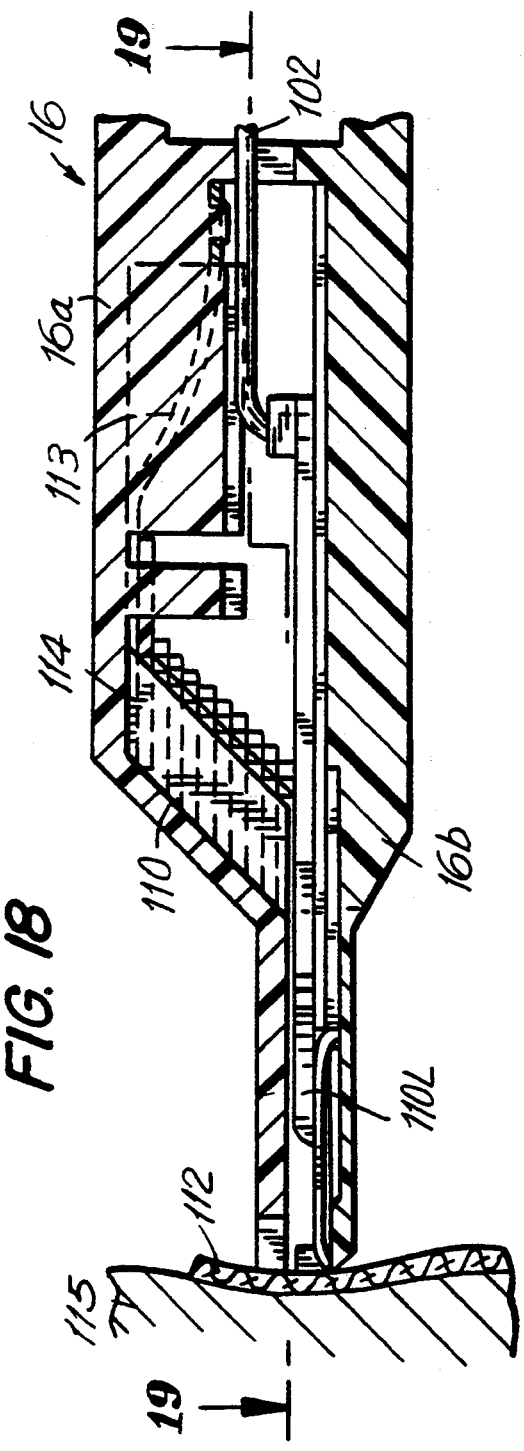
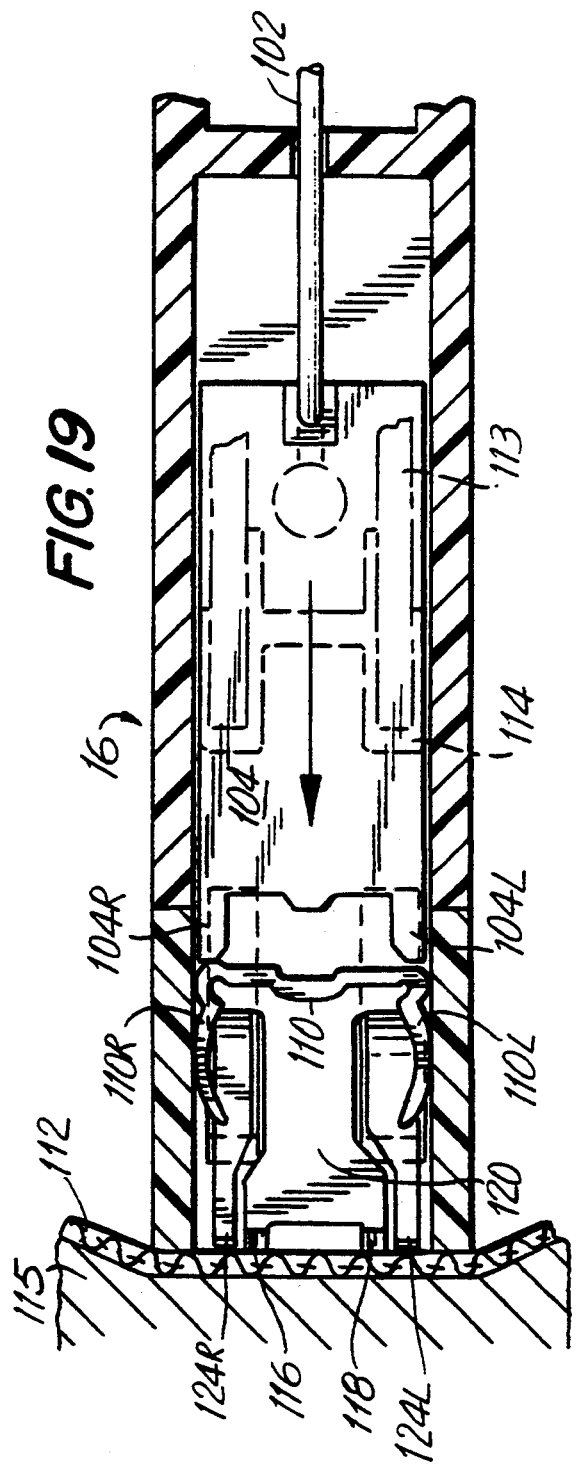

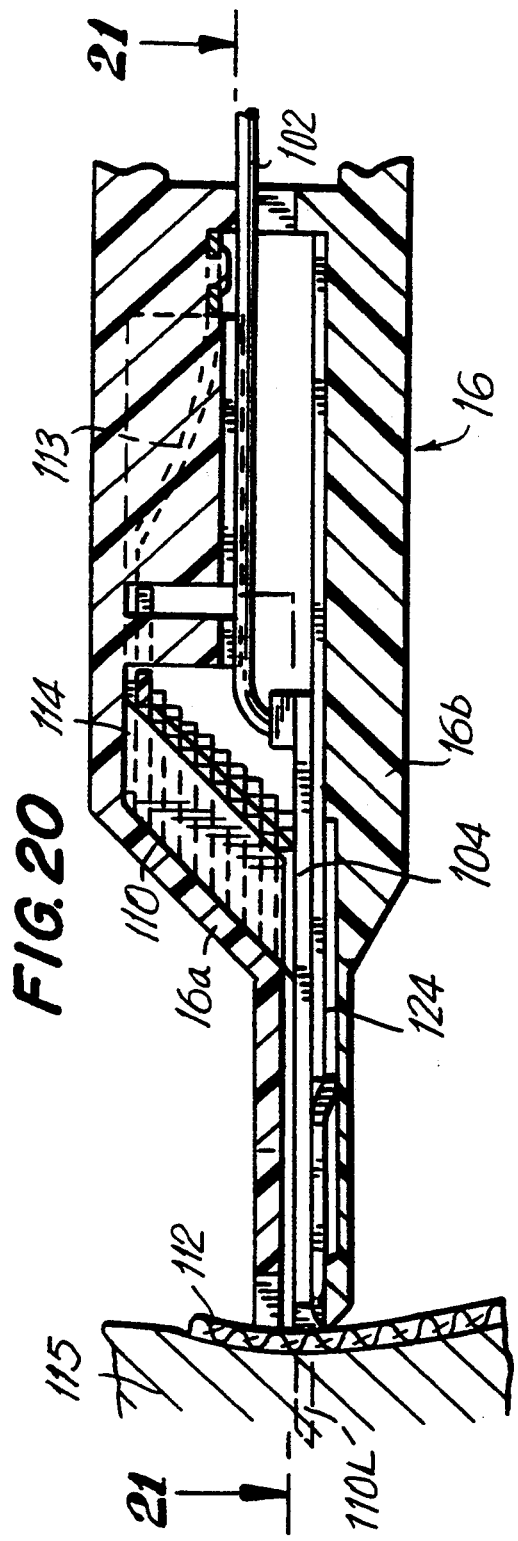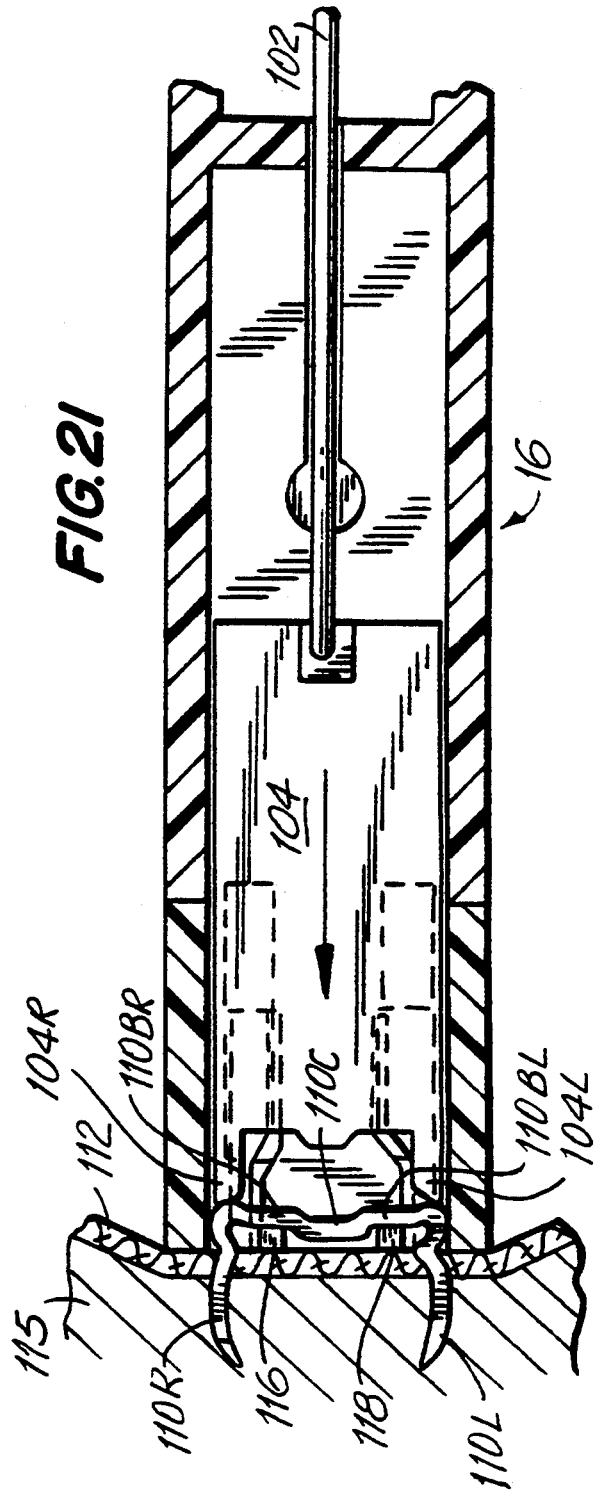

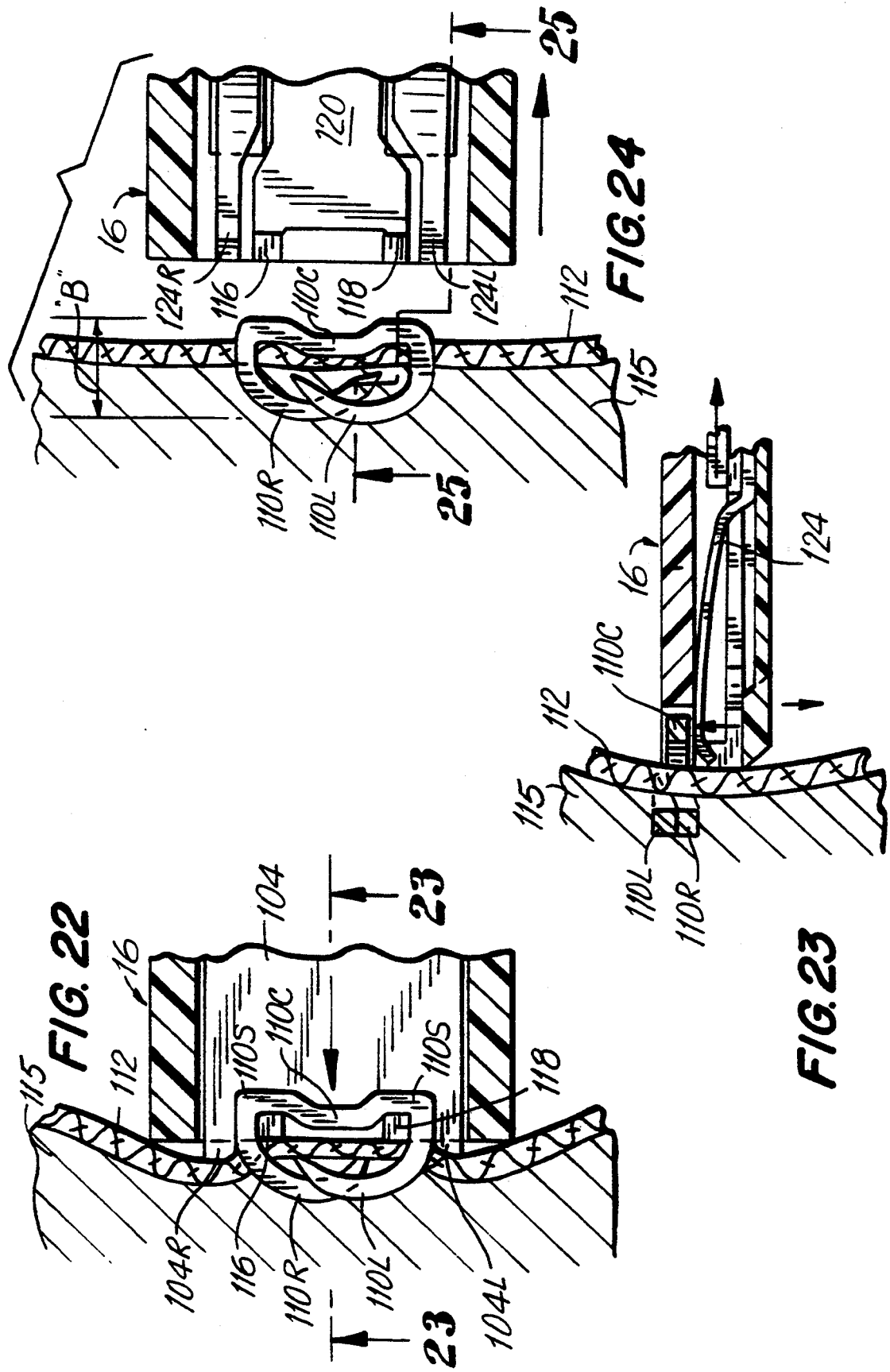

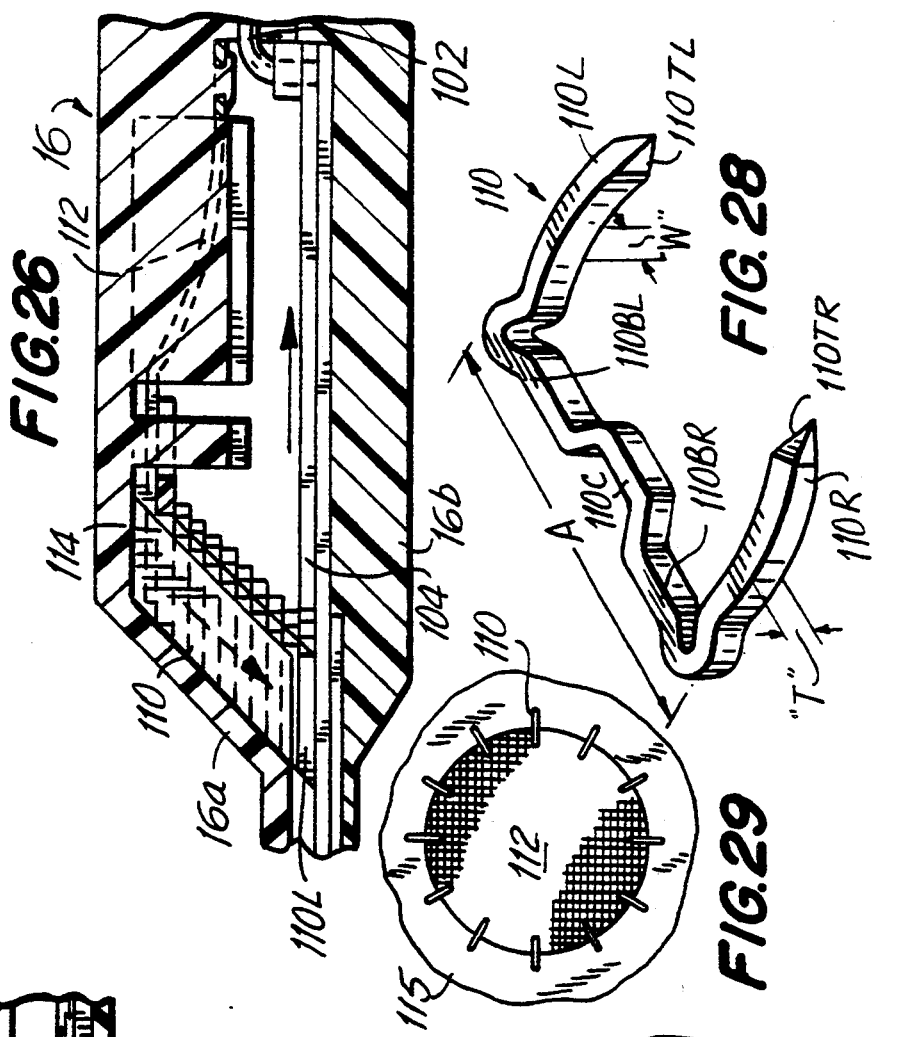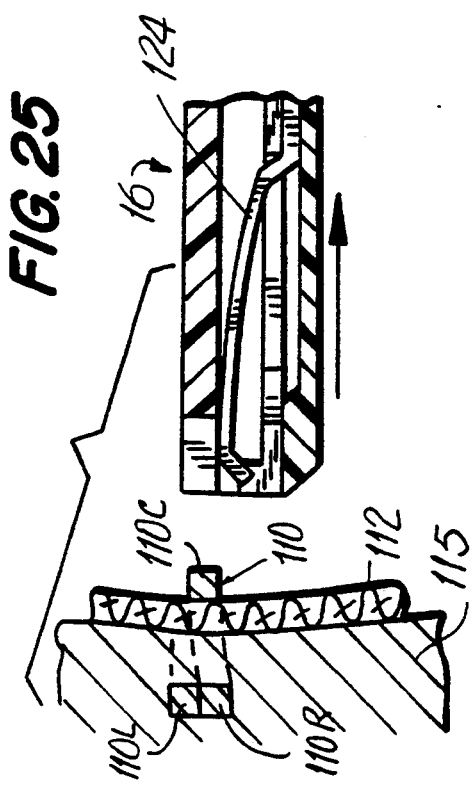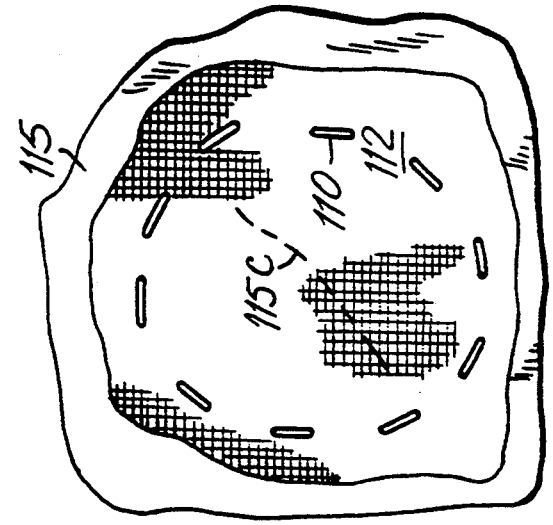

SURGICAL STAPLE FOR ATTACHING AN OBJECT TO BODY TISSUE

This is a divisional of copending application Ser. No. 07/782,290 filed Oct. 18, 1991 now U.S. Pat. No. 5,289,964.

BACKGROUND OF THE INVENTION

1. Field of the Invention

The present invention relates to an apparatus and method for applying surgical staples to attach objects to body tissue. More particularly, this invention relates to a staple applier particularly adapted for attaching surgical mesh to body tissue to reinforce a surgical repair of the body tissue, as in hernia repair.

2. Background of the Invention

Hernias may be divided into three general classes: direct hernia, indirect hernia and femoral hernia. In a direct or indirect inguinal hernia, often a part of the intestine protrudes through a defect in the supporting abdominal wall to form a hernial sac requiring surgery which generally includes a surgical incision in the groin ranging up to six inches in length. Several layers of the abdominal wall are generally separated to reach the herniated portions. During the procedure, the hernia is closed outside the abdominal wall in a manner which resembles the tying of a sack at the neck. Often a surgical mesh is attached by sutures directly over the hernia repaired opening to provide a reinforcement to the opening.

Traditionally, such hernia repairs involved major invasive surgical procedures which often caused excessive trauma to the patient and necessitated unusually long post-operative recuperative periods. In addition, numerous complications, related directly or indirectly to the surgery often resulted, including bleeding, infection, testicular atrophy, organ damage, nerve damage, blood vessel damage, etc. Further, cutting through the numerous layers of tissue to obtain access to the herniated area often caused severe trauma to the patient. A detailed discussion of traditional hernia repair may be found in "Hernia Repair Without Disability Second Edition" by Irving L. Lichtenstein.

Such invasive surgical procedures have also been utilized in other areas of the body, including surgery on the gall bladder, appendix, lungs and the like. For the reasons previously stated, the use of laparoscopic and endoscopic surgical procedures have been relatively popular and such popularity has provided additional incentive to develop the procedures further.

In laparoscopic procedures, surgery is performed in the interior of the abdomen through a small incision; in endoscopic procedures, surgery is performed in any hollow viscus of the body through narrow endoscopic tubes inserted through small entrance wounds in the skin. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues and vessels far removed from the incision, thereby requiring that any instruments be used in such procedures be long and narrow while being functionally controllable from one end of the instrument, i.e. the proximal end.

In hernia surgery, as compared to gall bladder surgery, certain procedures and instruments are the same, yet certain of the instrument requirements differ. For example, in hernia surgery a suitable mesh material is generally sutured over the opening in the tissue. The mesh material is often also attached by sutures and left within the opening to act as a reinforcing agent for tissue regrowth in the area of the surgery. One example of a mesh material currently utilized in hernia surgery includes a polypropylene material marketed by the Ethicon division of Johnson & Johnson, New Brunswick, N.J., under the trademark MARLEX. Another example of a mesh material is a tri-fluoroethylene material marketed by W. L. Gore & Associates, Newark, Del., under the trademark GORE-TEX.

As noted, during conventional invasive surgical procedures, such mesh materials are often sutured within the surgical opening or over the sutured opening by conventional suturing techniques. However, with the advent of laparoscopic surgery the need for suitable mesh attachment techniques through the relatively narrow endoscopic tubes or cannulas is clearly defined. Up to the present, such devices or staples suitable for mesh attachment have not yet been developed.

U.S. Pat. No. 4,944,443 to Oddsen et al. discloses an instrument and method for applying and forming staples into body tissue to suture a hernial opening. The staple is applied to two pieces of body tissue on opposite sides of the opening which are gripped, approximated and held together by a tissue positioning assembly. U.S. Pat. No. 4,919,152 to Ger relates to a surgical instrument for placing a single clip which is proposed for use in direct hernia repair for closing sacs having narrow neck openings.

Up to the present there remains a need for an apparatus which is particularly adapted to endoscopically apply staples for attaching objects such as surgical mesh to body tissue in a manner to positively secure the object to the body tissue without danger of separation thereof after the attachment is completed. The present invention relates to such an apparatus as well as a method for attaching such objects with staples particularly configured and adapted to accomplish these objectives.

SUMMARY OF THE INVENTION

An apparatus for endoscopic application of a surgical staple adapted to attach objects to body tissue, which comprises frame means, generally elongated endoscopic means connected to the frame means and extending distally therefrom, means for storing at least one surgical staple at the distal end portion, the staple configured and adapted to attach an object to body tissue, means for individually advancing the at least one staple distally for positioning adjacent the body tissue, and anvil means for closing the staple in a manner to encompass at least a portion of the object and to penetrate the body tissue to attach the portion of the object to the body tissue. Preferably, the apparatus for endoscopic application of surgical staples is adapted to attach surgical mesh to body tissue and comprises means for storing a plurality of surgical staples in generally stacked relation to permit configuring and dimensioning the endoscopic means for insertion into an endoscopic cannula tube. The staples are configured and adapted to attach the surgical mesh to body tissue, particularly for hernia related surgery. Further, the staple advancing system extends from the frame means to the endoscopic means and is activated by a trigger mechanism pivotally attached to the frame means and forming a part thereof.

The surgical staples are stored in stacked relation at the distal end of the endoscopic means. Also, the endoscopic means defines a longitudinal axis and the surgical staples are stacked to form an angle with the longitudinal axis, thereby improving visibility.

The surgical staple storing means is pivotally attached at the distal end portion of the endoscopic means wherein the surgical staple storing means is selectively pivotable by the user. Pivotal control means is located at the proximal end of the endoscopic section to pivot the surgical staple storing means from a proximal location. The location of the pivotal control means is provided for convenience and accessibility to the operator. The pivotal control means of the staple storing means comprises a member with respect to the endoscopic means in proximal and distal directions and adapted to position said surgical staple storing means at substantially zero degrees with respect to said longitudinal axis when said pivotal control means is in a first position and said surgical staple storing means forms an angle of up to about 45 degrees when said pivotal control means is in a second position.

The first position may be the proximalmost position of the pivotal control means and the second position may be the distalmost position corresponding to the staple storing means being pivoted up to about 45 degrees with respect to at least one side of the longitudinal axis. Further, the pivotal control means of the staple storing means may include a generally cylindrical movable member slidably positioned about a proximal portion of the endoscopic means.

The staple storing means may also comprise a rotatable sleeve positioned within the movable member and adapted to rotate in a first direction when the movable member is moved toward the proximalmost position and to rotate in the opposite direction when the movable member is moved toward the distalmost position.

The surface at the distalmost end portion of the rotatable sleeve may form an angle with respect to the longitudinal axis of the endoscopic means and the distalmost end surface of the rotatable sleeve may be positioned and arranged to engage elongated control means positioned within the endoscopic means for engagement with at least a portion of the staple storing means at a distal location of the endoscopic means whereby rotatable movement of said rotatable sleeve correspondingly produces longitudinal movement of said elongated control means. Preferably, the elongated control means comprises at least two elongated rods positioned within the endoscopic means and in engagement with the distalmost end portion of the rotatable sleeve at the proximal ends thereof and arranged to engage at least a portion of the staple storing means at respectively opposed locations such that rotation of the rotatable sleeve in a first direction produces distal movement of at least one of the rods and corresponding proximal movement of the other rod and rotation of the rotatable sleeve in the opposite direction respectively produces correspondingly respectively opposite movement of the rods.

The staple storing means includes an indentation adapted to receive each rod in engagement therewith and each rod is correspondingly configured at the distal end to engage the respective indentation to produce smooth rotation of the staple storing means when the rods are respectively moved distally and proximally. Further, the means for individually advancing the staples distally is user controllable at a proximal location. The means for individually advancing said staples distally comprises a plate member positioned adjacent and proximal of the lowermost staple and adapted to be movable distally whereby the plate member engages the lowermost staple and advances the staple in the distal direction. Also, the means to individually advance the staples comprises staple pusher means. The staple pusher means comprises the plate member and the plate member is dimensioned, configured and arranged to engage and advance each staple distally.

The staple pusher means includes an elongated member of super elastic material such as NITINOL brand metal and is adapted to advance the staples and transmit closing force thereto. This member is further adapted to resiliently deform to facilitate pivoting movement to the staple storing means. The staple pusher means further comprises an elongated staple firing rod.

In the preferred apparatus the staple pusher means is biased to a pre-fired position by a constant force negator spring which prevents the operator tendency to rotate the hand, which occurs when a spring force increases.

Also a trigger mechanism is pivotally mounted for pivotal movement against the force of the negator spring when pivoted proximally to a position corresponding to advancing the pusher means distally to advance the staple next in line for closure.

The staple storing means includes anvil means positioned distally of the stack of staples and configured, dimensioned and adapted to be engaged by each said staple when said staple is advanced distally by said plate member.

The staples are each formed of a first length of wire having at least two leg portions at each end extending generally perpendicular to said first length of wire. The anvil means comprises at least two upstanding leg members positioned to be engaged by the first length of wire of each staple when the staple is advanced distally by the plate member. The leg members of the anvil means are dimensioned, positioned and arranged such that engagement by the first length of wire of each staple causes the leg members of the staple to fold inwardly toward the first wire due to the configuration of the staple and the corresponding configuration of the distalmost staple engaging edge of the plate member. The plate member is connected to elongated means comprised of super elastic member and the firing rod.

The means to move the elongated means and the plate member in distal and proximal directions is positioned within the frame means. Resilient means is positioned below each staple such that upon completion of closure thereof, and withdrawal of the staple advancing plate member the resilient means resiliently lifts the staple above the level of the anvil means. Also, the elongated means extends from the frame means through the endoscopic means whereby a distal portion thereof and the plate member are positioned within the staple storing means. The means to advance the elongated means and the plate member includes ratchet and associated pawl means adapted to prevent proximal movement thereof except when the staple advancing means is advanced to the distalmost position whereby the pawl means is released so as to permit return of the elongated member and the staple advancing plate member to the proximalmost position to advance the next staple of the stack of staples.

Preferably, the ratchet and pawl means comprises a ratchet member fixedly connected to the frame means and has a ribbed surface, and pawl means connected to the elongated plate advancing means and positioned adjacent the ratchet member and adapted to engage the ribbed surface. The ribbed surface is correspondingly configured and dimensioned to prevent proximal movement of the pawl means when the elongated plate advancing means is advanced at least partially in the distal direction. The ribbed surface of the ratchet member is comprised of a plurality of substantially and successive V-shaped peaks and valleys and the pawl means is configured at one end portion to engage the peaks and valleys in a manner which permits distal slidable movement thereof but prevents proximal movement thereof. Also, means is provided to release the pawl means when the pawl means is in the distalmost position corresponding to the distalmost position of the plate member and closure of the staple has been completed. A finger operative lever is adapted to produce distal movement of the elongated member and the plate member when said lever is pivotally moved.

The frame means has a pistol-like shape and includes a first member having a distal end connected to the endoscopic means and a manually gripping member at the proximal end is adapted to be gripped manually by the user. The endoscopic means is rotatable about the longitudinal axis and the pivotal control sleeve of the staple storing means is connected for rotation with the endoscopic means such that rotation thereof produces corresponding rotation of said endoscopic means. As described hereinabove, distal and proximal movement thereof produces pivotal movement of the staple storing means. The staple storing means is adapted to be pivoted up to about 45 degrees with respect to each side of the longitudinal axis whereby full pivotal articulation thereof is provided of about 90 degrees.

A surgical staple is adapted to attach objects such as mesh materials to body tissue which comprises, a length of wire having a central portion, a wire leg member extending generally perpendicular to the central wire portion at each end portion and adapted to penetrate the object and body tissue when positioned in adjacent engaged relation therewith and advanced thereinto. A bridge portion connects the central wire portion to each leg member and has a first generally arcuate portion generally concave and facing in a direction generally toward the center of the central wire portion. The inwardly facing concave portions are connected to each leg member by an arcuate portion having a generally concave configuration in the opposite direction so as to respectively engagably support each bridge portion against a pair of anvil members whereby applying force to the bridge portions causes the leg members to bend inwardly toward the central wire portion at respective locations inward of the first mentioned arcuate portions in a manner to form an acute angle relative thereto. The maximum distance between the central wire portion and each folded leg member is sufficient to grip the object and to penetrate the body tissue sufficient to attach the object to the body tissue. Each leg member has a pointed tip to penetrate the object and the body tissue.

Each leg member of the staple has a tapered portion at the free end. The tapered portion on one leg member is located opposite the tapered portion on the other leg member whereby folding the leg members inwardly toward each other causes each tapered portion to respectively cam the other leg member whereby the leg members are folded toward each other in adjacent relation without interference with each other. The central wire portion is positioned inwardly of each bridge portion to facilitate gripping the object between the central wire portion and the leg members. Further, each leg member has a generally arcuate shape and has a concave portion thereof generally facing the other leg member. The surgical staple is preferably made of titanium. Also, the central wire portion includes a portion thereof which is positioned inwardly of the bridge portions in the body tissue gripping direction to thereby form a bight portion for gripping the object and body tissue in combination with the leg members.

A method is disclosed for endoscopically applying surgical staples to attach objects such as surgical mesh to body tissue comprising the steps of storing at least one surgical staple in endoscopic means having storing means positioned at the distal end portion and adapted for advancing and closing said staple, positioning the object adjacent the body tissue for attachment to the body tissue, and advancing the surgical staple distally so as to penetrate the object and the body tissue and to close the staple in a manner to attach the portion of the object to the body tissue. Preferably, a plurality of surgical staples are stored in stacked relation in the endoscopic means.

The invention relates to the combination of a cannula adapted for insertion into a body cavity, the cannula including valve means for sealing the cannula. An endoscopic surgical staple applier has a frame, and an endoscopic portion defining a longitudinal axis, and extending distally from the frame, the endoscopic portion configured and adapted for insertion into the cannula through the valve means in sealing engagement therewith. The endoscopic portion further includes a plurality of surgical staples in stacked relation, and means for individually pushing the staples through the distal end thereof is provided whereby staple closing means causes the staples to be closed while attaching an object such as surgical mesh to the body tissue. Seal means is positioned and adapted to obstruct passage of gaseous media from the body cavity.

A kit is also disclosed for endoscopic application of a surgical staple adapted to attach surgical mesh to body tissue in hernia repair, which comprises, surgical mesh, cannula means, and apparatus for endoscopic application of a surgical staple adapted to attach the surgical mesh to body tissue. The apparatus and staples of the kit are constructed according to the invention. The components may be supplied as part of a kit or they may be packaged in a blister-type or other package.

BRIEF DESCRIPTION OF THE DRAWINGS

Preferred embodiments of the invention are described hereinbelow with reference to the drawings wherein:

FIG. 1A is a perspective view of the distal end portion of the apparatus of FIG. 1 illustrating an alternative embodiment for pivoting the staple storage magazine;

FIG. 3 is a cross-sectional view taken along lines 3—3 of FIG. 1, illustrating the handle mechanism of the instrument in the pre-fired condition;

FIG. 4 is a cross-sectional view taken along lines 4—4 of FIG. 3 illustrating the mechanism at the proximal end of the instrument for providing controlled distal movement to advance and to close staples at the distal end;

FIG. 5 is an enlarged cross-sectional view of the pawl and ratchet system in the handle which prevents proximal movement of the staple advancing system after distal movement has begun;

FIG. 6 is a view similar to FIG. 5 illustrating the pawl and ratchet system of FIG. 5 after a staple has been fired and during the proximal movement of the firing mechanism;

FIG. 7 is a cross-sectional view similar to FIG. 3 with the staple advancing actuating handle in the full proximal pivoted position corresponding to firing of a staple;

FIG. 8 is an enlarged cross-sectional view taken along lines 8—8 of FIG. 1 illustrating the rotating mechanism for the endoscopic portion and the system for pivoting the staple storage magazine from the proximal end;

FIG. 9 is a cross-sectional view taken along lines 9—9 of FIG. 8;

FIG. 10 is a cross-sectional view taken along lines 10—10 of FIG. 8 illustrating the system for providing pivotal motion of the staple storage magazine located at the distal end;

FIG. 11 is a cross-sectional view taken along lines 11—11 of FIG. 9 illustrating further details of the system for providing pivotal motion to the staple magazine at the distal end;

FIG. 12 is a view of the interior surface of the inner sleeve of the manually operable collar of FIGS. 8–11, projected as a flat surface to illustrate the helical groove provided for coaction with a pin to provide pivotal motion for the staple magazine at the distal end;

FIG. 13 is a perspective view of an internal sleeve and pin which coacts with the inner sleeve shown in FIGS. 11 and 12 which forms part of the system for pivoting the staple magazine at the distal end;

FIG. 15 is an exploded perspective view with parts separated, of the staple storage magazine which is controllably pivotally mounted at the distal end portion of the endoscopic section;

FIG. 16 is a cross-sectional view taken along lines 16—16 of FIG. 1 illustrating the distal end of the instrument including the pivotal staple magazine at three positions;

FIG. 17 is a cross-sectional view taken along lines 17—17 of FIG. 16 illustrating the staple next in line and the pusher plate provided for advancing the staple toward a staple closing anvil;

FIG. 18 is a cross-sectional view of the distal end of the instrument shown in engagement with a surgical mesh positioned against body tissue prior to firing the staple;

FIG. 19 is a cross-sectional view taken along lines 19—19 of FIG. 18;

FIG. 20 is a cross-sectional view similar to FIG. 18 during the firing of the staple and after penetration into the mesh and body tissue, but prior to closure;

FIG. 21 is a view similar to FIG. 19, taken along lines 21—21 of FIG. 20;

FIG. 22 is a cross-sectional view of the distal end of the instrument of the invention after closure of the staple in position to attach the surgical mesh to the body tissue;

FIG. 23 is a cross-sectional view taken along lines 23—23 of FIG. 22 illustrating the staple ejection system for releasing the closed staple from the anvils after firing;

FIG. 24 is a cross-sectional view similar to FIG. 22 illustrating the staple after closure about the surgical mesh and body tissue and the distal end of the instrument withdrawn from the surgical mesh;

FIG. 25 is a cross-sectional view taken along lines 25—25 of FIG. 24;

FIG. 26 is a cross-sectional view of the distal end portion of the staple storing magazine of the instrument after firing a staple;

FIG. 27 is a frontal view of a repair in body tissue illustrating one example of an arrangement of staples of the invention for attachment of reinforcing surgical mesh to the tissue;

FIG. 28 is a perspective view of a staple constructed according to the invention for attaching surgical reinforcing mesh to body tissue over a surgical repair; and FIG. 29 is another example of arranging the staples for attachment of the reinforcing surgical mesh to the body tissue in the area of a hernia repair.

DETAILED DESCRIPTION OF THE PREFERRED EMBODIMENTS

General

In general, the objective of the apparatus is to store a plurality of staples in the magazine as will be described in greater detail, and to individually advance each staple distally for closure about anvils while attaching a surgical mesh to the body tissue.

Following a general description of the present instrument, the description will be divided into separate sections to describe the structure and the desired movements produced thereby. Those sections include the handle section, the staple storage magazine pivoting system, the endoscopic section and staple firing system, the staple storage magazine, the staple closing system and the inventive staple. Also a kit for attaching objects such as surgical mesh is described.

The Instrument

Figure 1:
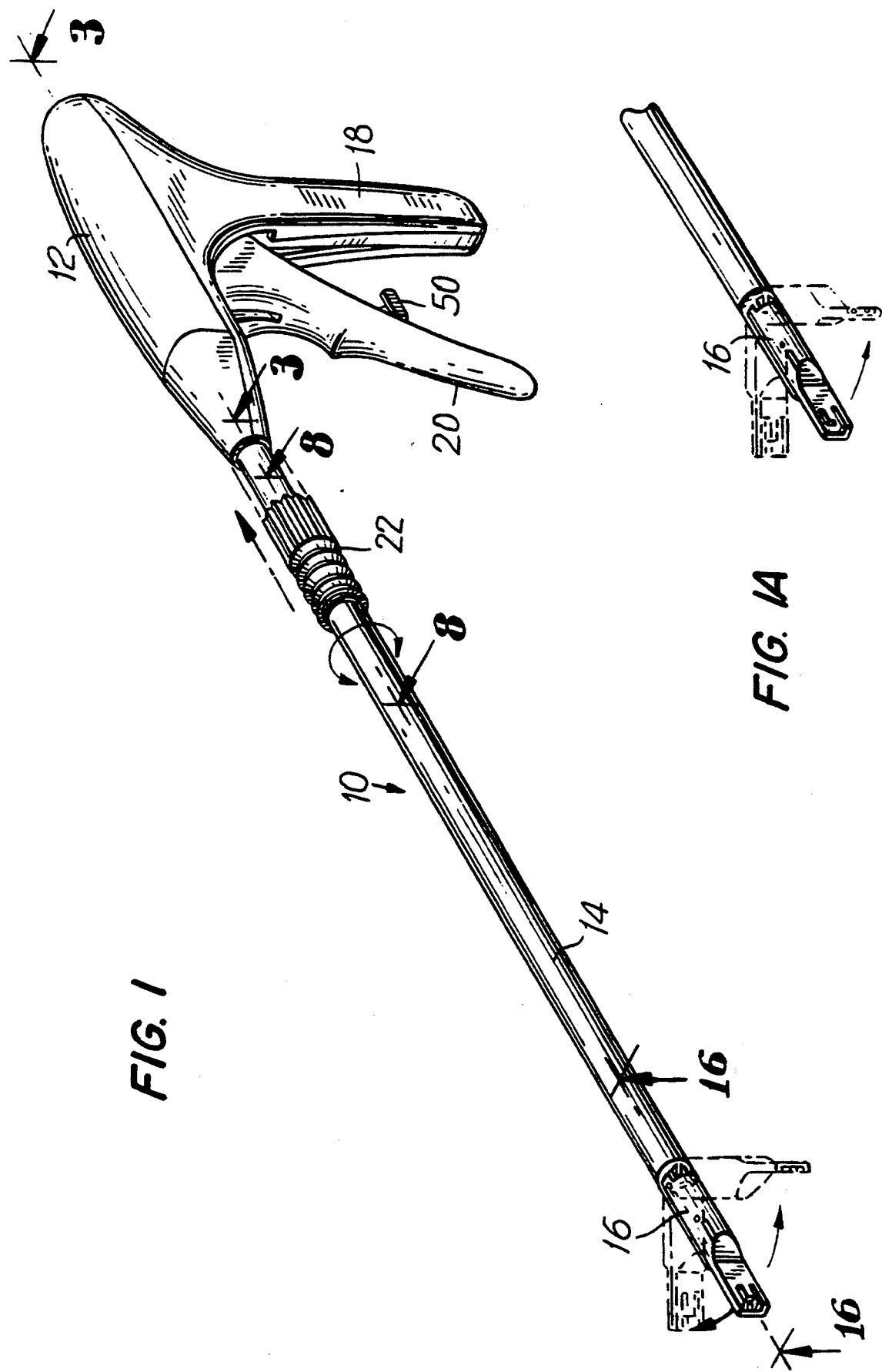
FIG. 1 is a perspective view from above, of an apparatus constructed according to the present invention for applying surgical staples to attach objects to body tissue.

Referring initially to FIG. 1 there is illustrated in perspective view the apparatus 10 particularly adapted for endoscopic application of surgical staples to attach surgical mesh to body tissue during hernia repair. Except where noted otherwise, the materials utilized in the components of the apparatus generally include such materials as polycarbonate for housing sections and related components, and stainless steel for such components which transmit forces. One preferred polycarbonate material is LEXAN brand polycarbonate available from General Electric Company. Other specific preferred materials such as nylon or glass filled nylon (for strength) are also utilized. However, equivalent alternative materials will readily come to the mind of those skilled in the art.

The apparatus 10 includes handle portion 12, and endoscopic section 14 having at the distal end portion a staple storage magazine 16 which pivots with respect to at least one side of the longitudinal axis extending centrally through the endoscopic section as shown in FIG. 1. Generally, staple storage magazine 16 will selectively pivot up to about 45 degrees with respect to the aforesaid longitudinal axis. In the illustration of FIG. 1 the staple storage magazine 16 is shown in general alignment with the longitudinal axis of the endoscopic section and in phantom to illustrate a range of movement. The total range of pivotal motion of the staple storage magazine 16 as shown is approximately 90 degrees, i.e. 45 degrees to each side of neutral.

Referring generally to FIG. 1, the handle 12 of instrument 10 includes manual grip 18 and pivotal trigger 20 which is pivoted toward and away from manual grip 18. Trigger 20 is pivoted toward manual grip 18 during the staple advancing and firing sequence which will be described in further detail. Trigger 20 pivots away from manual grip 18 to return the instrument to the pre-fired condition in position for firing the staple next in line.

A double knurled finger operative collar 22 is rotatable and adapted to rotate the entire endoscopic section 14 a full 360 degrees as will be described hereinbelow, while proximal movement of the finger collar 22 produces pivotal motion of the staple storage magazine to one of the positions shown in phantom in FIG. 1. To achieve the other position shown in phantom in that FIG., the collar 22 may be simply rotated 180 degrees thereby rotating the entire endoscopic section and causing the position of the magazine 16 to be reversed as shown to the other position shown in phantom. Thus, it can be seen that the combination of full rotation of the endoscopic section and the pivotal movement of the staple storing magazine facilitates a wide range of articulation of the distal end of the staple magazine 16, thus facilitating application of staples over a wide range of locations (±180 degrees) and in any of a plurality of orientations. In the embodiment of the invention shown in the FIGS., when the collar 22 is moved to its proximalmost position the staple magazine is in one of the positions shown in phantom in FIG. 1, i.e. at an angle with respect to the longitudinal axis of the instrument. When the collar 22 is advanced to the distalmost position the staple magazine assumes the position shown in FIG. 1, i.e. in alignment with the longitudinal axis of the instrument.

Thus, in the preferred embodiment of FIG. 1, it can be seen that the full 90 degrees of movement of the magazine may be achieved simply by longitudinal movement of collar 22 in combination with full rotation of the endoscopic section. The longitudinal movement of collar 22 causes pivotal movement of the staple storing magazine to 45 degrees in one direction and rotation of the endoscopic section provides completion of the articulation of the magazine. Both of these movements in combination, facilitate a wide range of maneuverability of the distal end of the staple magazine 16, thus facilitating application of staples over a wide range of locations (±180 degrees) and in any of a plurality of orientations.

Alternatively, the positions of the staple storing magazine 16 may be achieved as shown in FIG. 1A, i.e. by movement of the magazine between zero degrees and about 45 degrees on either side of the longitudinal axis. In such arrangement, to achieve the positions shown in phantom in FIG. 1A, the collar 22 is moved distally and proximally, equal distances on either side of a neutral detent. Movement in one direction would pivot the magazine to one side and movement in the other direction would cause pivotal movement of the magazine in the opposite direction. The directions selected would be arbitrary. However, in this last described embodiment the orientation of the magazine would be the same throughout the 90 degree pivoting range, whereas in the preferred embodiment of FIG. 1, the orientation of the magazine when on one side is opposite the orientation when on the other. Further, in this embodiment the endoscopic section will be somewhat longer to accommodate the additional movement of collar 22.

The Handle Section

Figure 2:
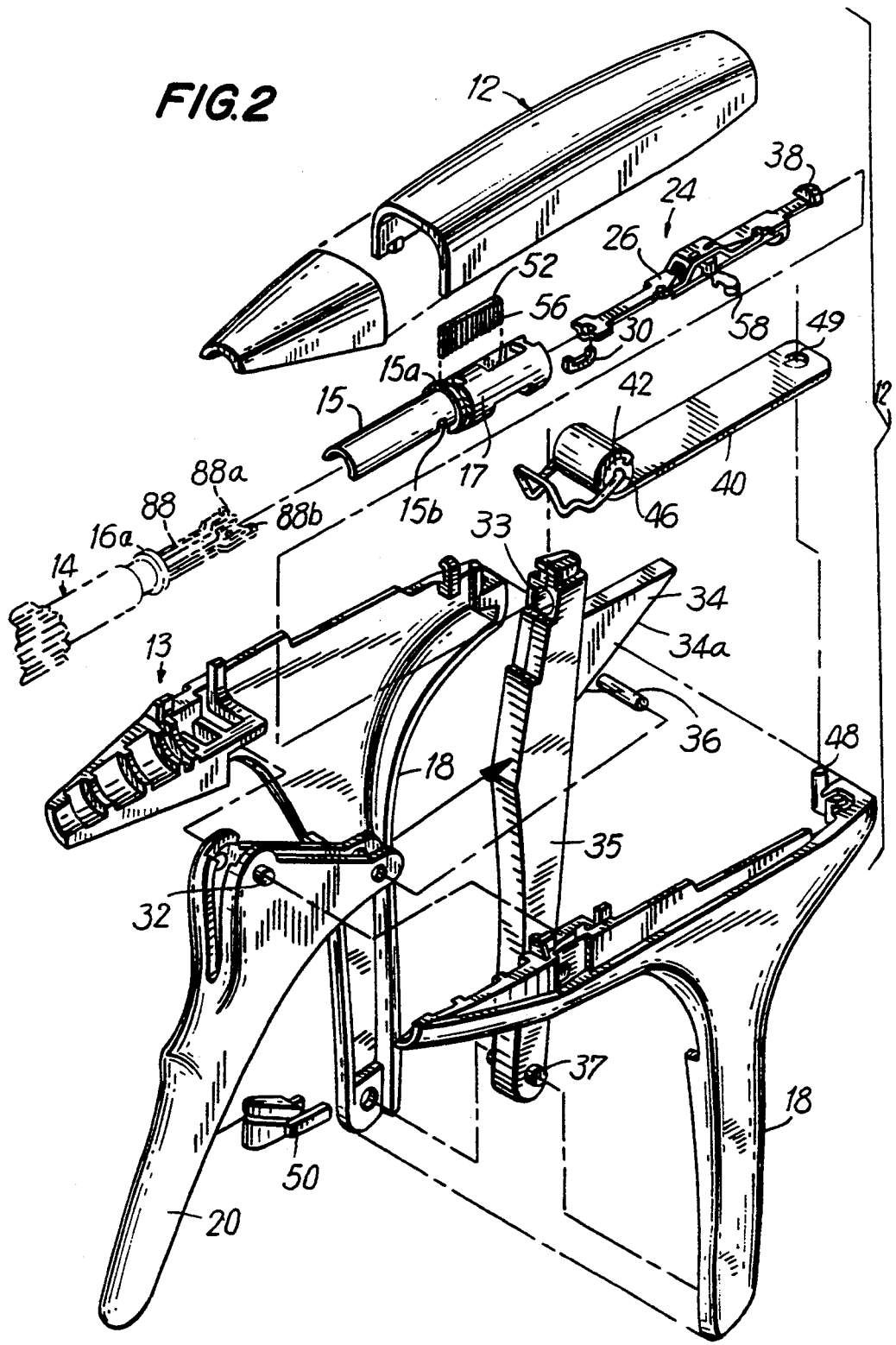
FIG. 2 is an exploded perspective view with parts separated, of the handle of the instrument of the invention and the associated components.

Referring to FIG. 2, there is shown an exploded perspective view with parts separated, of the handle of the instrument with associated components. The handle is comprised of an outer housing preferably formed of separate sections as shown, of polycarbonate material. The separate parts shown are attached by welding, adhesives, etc. FIG. 3 illustrates a cross-sectional view of the handle mechanism taken along lines 3—3 of FIG. 1. The ultimate purpose of the handle mechanism is to provide controlled distal movement to the pusher assembly 24, a portion of which is shown in FIG. 2. The pusher assembly extends through the endoscopic section 14, a portion of which is shown in phantom in FIG. 2. In the embodiment shown, the endoscopic section shown is intended to be permanently and rotatably attached to the instrument via rim 16a formed at the proximal end of endoscopic section 14 and rim 15a on half round sleeve 15. The instrument shown is contemplated to be entirely disposable. Half round sleeve 15 is integrally formed with barrel 17 which is in turn affixed to handle 12 at the nose piece 13.

However, it is also contemplated and within the scope of the invention to construct the endoscopic section to be selectively detachable whereby the handle may be sterilized and reused, or the endoscopic section can be sterilized, and the staple storage magazine reloaded with staples for re-use. Alternatively a replacement staple magazine, and optionally a replacement endoscopic section, may be detachably secured to a disposable handle for multiple use during a single surgical procedure. Thus, any combination of alternatives may be incorporated within the scope of the invention.

Figure 14:
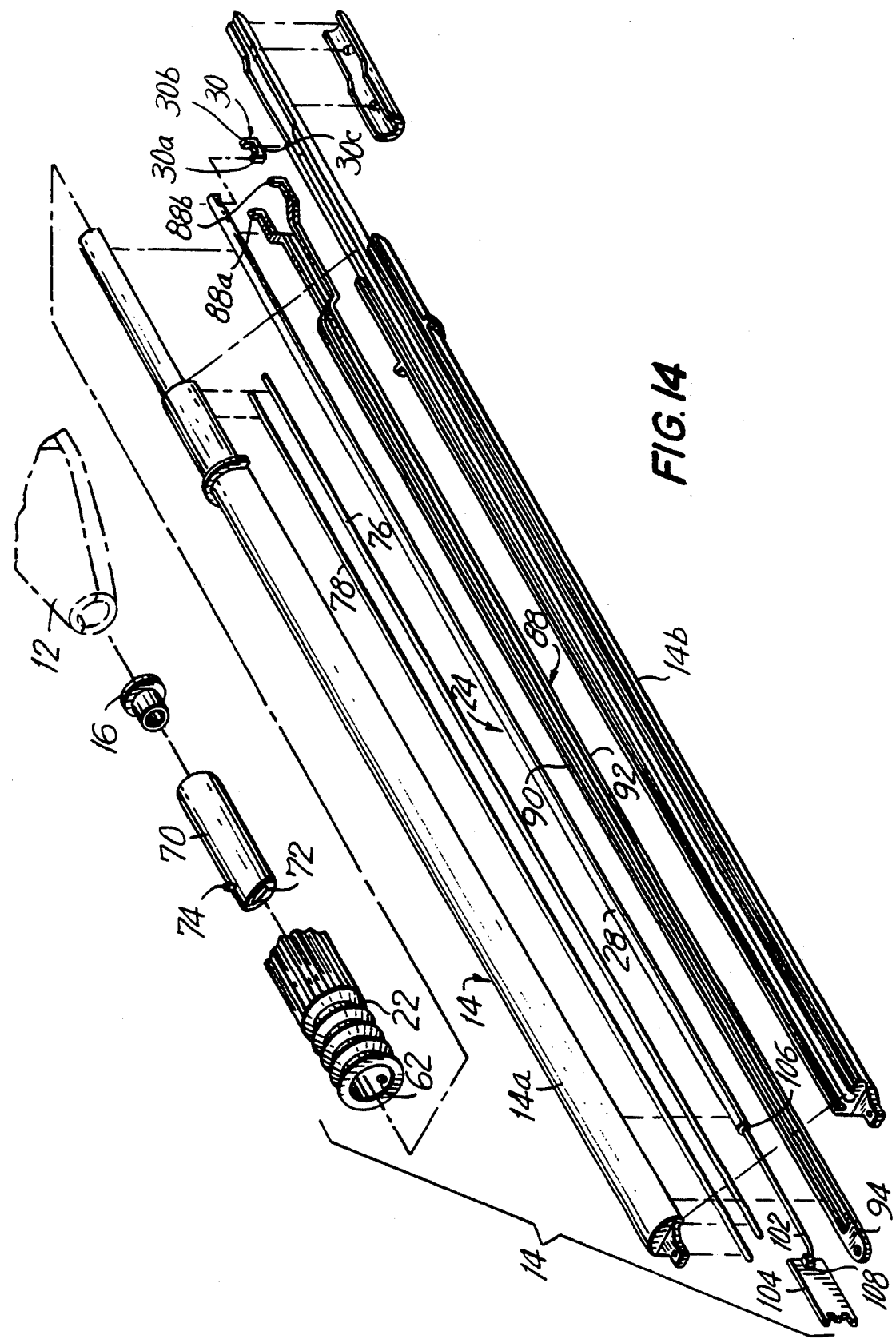
FIG. 14 is an exploded perspective view with parts separated, of the endoscopic section of the instrument of the invention, illustrating the staple advancing system and components thereof.

Referring now to FIG. 2 in conjunction with FIGS. 3, 7 and 14, pusher assembly 24 includes flanged thrust bar 26 connected to firing rod 28 by lost motion connector 30 as shown in FIG. 3. Lost motion connector 30 is a bar having a generally "U-shaped" configuration as shown. The lost motion connector 30 provides a positive connection between flanged thrust bar 26 and firing rod 28, yet provides a small space between the firing rod and the thrust bar 26 as will be described. Since the respective slots 28a and 26a in the firing rod 28 and in the thrust bar 26 are dimensioned slightly larger in width than the thickness of the legs 30b and 30c of the lost motion connector 30 which are received in these slots, a small degree of relative movement (i.e., about one tenth (1/10) of an inch) is provided permitted between the components in the staple firing chain. This small degree of movement is provided for several reasons as follows: 1) minor pivotal proximal movements of the trigger mechanism will not immediately result in engagement between the pusher assembly and the staple next in line, thus avoiding inadvertent distal movement of the staple during handling by operating room personnel, or positioning by the user; 2) engagement of the pusher assembly with the next staple will not occur until the pawl and ratchet plate of the clutch mechanism (described hereinbelow) takes place, thus preventing inadvertent partial advancement of several staples at a time. This would occur if the operator were allowed to partially activate the trigger mechanism several times over the same part of its cycle. The clutch mechanism prevents such movements. Further, this free movement of the thrust bar 26 also permits the staple advancing and forming components to engage each other smoothly without jamming or intercomponent interference with themselves and with the components of the system for pivoting the staple storage magazine 16 as will be described hereinbelow. Explanation of the pivoting system for the staple storage magazine will illustrate the advantages of the lost motion connector bar in further detail.

Trigger mechanism 20 is pivotally attached at pivot pin 32 for pivotal movement toward and away from handle grip 18, and is adapted to produce upward and downward rotational movement of triangular member 34 when horizontal pin 36, attached to trigger mechanism 20, traverses an upward arc whose center of rotation is located at pivot pin 32. Thus, it can be seen that when handle grip 18 is positioned in the palm of the user's hand and trigger mechanism 20 is squeezed toward handle grip 18, horizontal pin 36 traverses an upward arc while engaging the longer side 34a of triangular member 34 as shown. This movement causes triangular member 34 to rotate upward in a counter-clockwise direction while upright member 35 to which it is attached, pivots forwardly about a point of rotation defined by pivot pin 37 located at the lowermost end of a handle grip 18 shown in FIG. 2.

As can be seen in FIGS. 2 and 3, pusher assembly 24 is connected to upright member 35 through aperture 33 such that inward squeezing of trigger mechanism 20 will cause the entire pusher assembly to advance distally against the constant force provided by negator spring 40 as shown. The negator spring 40 is formed of a resilient flat spring material coiled about the rotational bar 42 which is rotationally mounted about cross member 44 which forms part of bracket 46. The free end of negator spring 40 is attached to an anchor pin 48 via aperture 49 as shown, while the spring 40 is normally biased toward the coiled configuration as shown in FIG. 3. It can therefore be appreciated that after squeezing trigger mechanism 20 the full stroke from the position shown in FIG. 3 toward handle grip 18 to the position shown in FIG. 7, release of the trigger mechanism will permit the negator spring 40 to assume control and to return rotational bar 42 to the pre-fired proximal location by the automatic winding action of the negator spring 40 to its original unloaded configuration. This motion in turn causes the entire pusher assembly 24 to return to the proximalmost pre-fired position as shown in FIG. 3. The constant force of negator spring 40 uniquely prevents the natural tendency of the user to rotate the hand as with springs which increase in force when progressing through a full spring cycle.

Referring once again to FIGS. 2 and 3, trigger stop device 50 is attached to trigger mechanism 20 and is configured and dimensioned for engagement with handle grip 18 in a manner to thereby limit the proximal pivotal movement of trigger mechanism 20. Depending upon the particular limits required in the apparatus, trigger stop device 50 can be dimensioned accordingly.

Referring now to FIGS. 4–6, the structure and function of the uni-motion clutch mechanism will be described. This clutch mechanism prevents proximal movement of the pusher assembly in the event the trigger mechanism is released after the squeezing motion of the trigger mechanism and the advancement of the pusher assembly has begun but before the full stroke is completed. The clutch mechanism is self-releasing when the pusher assembly reaches the distalmost position, thus permitting the entire pusher assembly to return to the pre-fired, or proximalmost condition, and the trigger mechanism to also return to the pre-fired position.

Referring now to FIG. 4 in conjunction with FIGS. 5 and 6, ratchet plate 52 is fixed to barrel 17 and therefore fixed with respect to the handle housing and possesses a surface defined by a plurality of right angle triangular shaped parallel ridges 56 as shown in FIGS. 4–6. Pawl 58 is rockably mounted for distal and proximal movement with pusher assembly 24 through barrel 17, and is biased toward ratchet plate 52 by resilient wire spring 60 as shown. The location of pawl 58 shown in FIG. 4 corresponds to the pre-fired condition of the apparatus with negator spring 40 in the fully wound position and pawl 58 located proximal of ratchet plate 52. Further, pawl 58 is preferably of stainless steel while ratchet plate 52 is made of brass or other compatible material.

While trigger mechanism 20 is squeezed toward handle grip 18 producing distal motion of the entire pusher assembly 24, pawl 58 engagably slides distally past the ratchet surface 56 of ratchet plate 52 as shown in FIG. 5 such that one corner of the tip 62 of the pawl 58 sequentially engages each right angled ridge of ratchet plate 52 to thereby prevent proximal movement of the pusher assembly in the event the trigger mechanism is released by the operator. The engagement of pawl 58 with ratchet plate 52 provides audible confirmation that the pusher assembly is moving distally since the user will hear a series of progressive audible clicks. This action—which is best shown in FIG. 5—continues with the tip 62 of pawl 58 sliding past the ratchet surface of the ratchet plate 52 until the pawl is positioned distally of the distalmost tooth.

After completion of the staple firing stroke and upon release of the trigger mechanism 20 the pawl 58 moves proximally with the pusher assembly as described under the action of spring 40. The end portion 62 of pawl 58 which is now free, engages the distal end of the ratchet plate 52 causing the pawl to rock to the reverse direction shown in FIG. 6 so as to slide proximally past the ratchet surface of ratchet plate 52 without interference to the proximal movement of the pusher assembly 24. Thus, it can be seen that the clutch mechanism as described will effectively permit squeezing the trigger mechanism 20 toward the handle grip 18 while maintaining all positions midway through the stroke in the event the operator releases the grip, while permitting return motion thereof after the stroke has been completed. The clutch mechanism also allows the operator to advantageously preposition a staple such that the legs of the staple protrude from the distal end of the staple magazine discussed hereinafter, and then to release pressure from the trigger mechanism. The operator may then turn full attention to locating the prepositioned staple in the desired target location, at which point the pivoting of the trigger mechanism may be resumed and the cycle completed. This staple prepositioning greatly facilitates staple placement.

The Staple Storage Magazine Pivoting System

Referring to FIGS. 8-14, the system for pivoting the staple storage magazine located at the distal end of the endoscopic section 14 will now be described. FIG. 8 illustrates double knurled finger operable collar 60 which is mounted for rotation with the endoscopic section 14 by inwardly extending pin 62 which is slidably positioned within longitudinal groove 64 in the outer housing half section 14a of endoscopic section 14, as shown in further detail in FIG. 14. Thus collar 60 is readily slidable distally and proximally while pin 62 slides within groove 64. Thus while permitting slidable movement of collar 60, pin 62 prevents independent rotation of collar 60 relative to the endoscopic section 14. Accordingly, when collar 60 is gripped between the user's fingers and rotated, the endoscopic section 14 rotates with the collar.

Positioned within finger operable collar 60 is helically grooved inner sleeve 66 fabricated of a suitable plastic material such as nylon, glass filled for strength. Helically grooved inner sleeve 66 is generally cylindrical in shape and includes a helical groove 68 shown in phantom lines in FIG. 8 and illustrated schematically in the projected frontal view of the sleeve shown in FIG. 12. The sleeve 66 is fixedly attached to outer collar 60 for rotation therewith. In the projected view of FIG. 12, the helical groove appears as a diagonal groove having a linear shape. In FIG. 11, finger operable collar 60 is shown in cross-section and the inner helically grooved sleeve 66 is shown whereby helical groove 68 is represented at two locations as viewed in FIG. 11. In FIG. 11, the cross-section of groove 68 at the 10 o'clock position (where lines 11—11 are located in FIG. 9) is just distal of the cross-section of groove 68 shown in phantom at the 12 o'clock position.

Referring now to FIG. 8 in conjunction with FIGS. 9-13, elongated internal cylindrical sleeve 70 is positioned partially within inner helically grooved sleeve 66 and collar 60 when collar 60 is in the distalmost position, as shown in FIG. 8; however, when collar 60 is withdrawn to the proximalmost position as shown in phantom lines in FIG. 8, the major portion of internal cylindrical sleeve 70 is positioned within collar 60 as shown. Internal sleeve 70 is preferably of nylon (preferably glass filled for strength) and defines a distal face 72 which is generally oriented at an acute angle with respect to the longitudinal axis of the instrument as shown clearly in FIGS. 8 and 13. The sleeve 70 contains pin 74 extending radially outwardly from the outer surface as shown. Pin 74 is preferably of steel or it may be formed of nylon integral with sleeve 70. Pin 74 is positioned for slidable movement within the helical groove 68 of inner sleeve 66 of collar 60 such that proximal movement of collar 60 will cause pin 74 to follow the groove 68 causing sleeve 70 to rotate in one direction. Similarly, distal movement of collar 60 to the position shown in phantom lines in FIG. 7 will cause pin 74 to traverse groove 68 in the opposite direction thereby causing sleeve 70 to rotate in the opposite direction.

The significance of the rotational motion of sleeve 70 as it pertains to the pivotal motion of staple storing magazine 16 will be described in further detail hereinbelow. At this stage, however, it is sufficient to state that the obliquely oriented distal face 72 of sleeve 70 engages the proximal ends of a pair of longitudinally extending push rods 76,78 shown in phantom lines in FIG. 13 and more clearly in FIG. 14 such that when collar 60 is moved distally or proximally, inner sleeve 70 also rotates and the rods 76,78 respectively move in equal and opposite directions by the engagement with different portions of oblique distal face 72 with these rods. In essence, one rod is engaged by a surface portion distal of the surface portion on the side of face 72 which engages the other rod. Thus, when the sleeve 70 is rotated in one direction, rod 78 moves in the distal direction while rod 76 withdraws proximally the same distance, and when sleeve 70 is rotated in the opposite direction, rod 76 moves in the distal direction and rod 78 moves proximally the same distance.

Collar 60 contains rotary ridges 60a in the distal half and longitudinal ridges 60b in the proximal half, and is thus conveniently movable longitudinally and rotatably by the user when the appropriate knurled portion is gripped between the user's fingers. However, the operator need not grip the collar 60 at any specific locations. The ridges may be formed integral by molding procedures or alternatively may be in the form of knurled surfaces. The rotary ridges respectively permit collar 60 to be finger movable distally and proximally, while the longitudinal ridges assist in rotation of collar 60 by hand. Rotational motion of the collar causes the endoscopic portion 14 to rotate while proximal movement of the collar in a preferred embodiment causes staple storing magazine 16 to pivot up to about 45 degrees in one direction with respect to the longitudinal axis of the instrument as shown in FIG. 1. Distal movement of the collar 60 to the distalmost position shown in FIG. 8, causes staple storing magazine 16 to withdraw to the original orientation shown in FIG. 1 which is generally in line with the endoscopic section. Thus, by pivoting the staple storing magazine up to 45 degrees and by rotating the endoscopic portion 14, the total range of movement of the staple storing magazine is 45 degrees to either side of the endoscopic section traversing a total of 90 degrees of effective pivotal movement. With respect to movements of collar 60, the direction which produces pivotal motion of staple storage magazine 16 away from the longitudinal axis or toward the axis is clearly a matter of choice and would be determined by the respective configurations of the coacting components.

In the alternative embodiment shown in FIG. 1A, the internal sleeve 70 and forward face 72 are configured such that collar 60 may be positioned midway between proximal and distal positions. The mid-position will correspond to the staple storage magazine being at zero degrees with respect to the longitudinal axis. Collar movement in one direction from neutral will produce up to 45 degrees of pivotal movement of magazine 16 and collar movement in the other direction on the side of neutral will produce pivotal movement of the magazine 16 up to 45 degrees in the other direction. A major distinction in this embodiment is that the actual orientation of the magazine with respect to the longitudinal axis will differ on either side of neutral.

Referring now to FIGS. 15 and 16, the system for providing pivotal motion to the staple storing magazine 16 is illustrated at the distal end of the instrument. In FIG. 16 the staple storage magazine 16 is shown in the position generally in alignment with the endoscopic section and is shown in phantom lines at the pivoted locations corresponding to plus or minus 45 degrees. The staple storage magazine is formed of an outer housing of a suitable plastic material such as polycarbonate and is comprised of upper housing half section 16a and lower housing half section 16b attached by welding, adhesives, etc. The upper housing half section 16a contains an indentation 80 at the proximal end having a "V-shaped" cross section and the lower housing half section 16b contains a similar indentation 82 also having a "V-shaped" cross section as shown. Both indentations 80,82 are adapted to respectively engagably receive the distal ends of rods 76,78 (which are rounded) such that when the rods are respectively and alternately moved in the proximal and distal directions as described hereinabove, one rod may advance distally to cause the upper housing to rotate and the other rod withdraws to permit the pivotal motion of the staple magazine. For example, as shown in FIG. 16, when rod 78 moves distally, engagement of the tip of the rod 78 with indentation 80 in upper housing 16a of staple storing magazine causes the staple magazine to pivot downwardly as shown in phantom.

Similarly, equal and oppositely withdrawing rod 76 will accommodate the downward movement of the staple storing magazine 16. In a similar fashion when the collar 60 is moved in the opposite distal direction the movement of each rod is respectively reversed causing rod 76 to move distally and to engage the lower housing 16b of staple storing magazine 16 and rod 78 withdraws to accommodate the pivotal movement of staple storing magazine back to the original (or neutral) position in general alignment with the endoscopic section as shown in FIG. 16. The lost motion connector 30 clearly provides a minor degree of space (i.e. about 1/10 inch) between the components, which space provides the advantages mentioned previously.

Alternatively one rod may be provided and connected to the staple storage magazine and adapted to pivot the magazine by causing such rod to move proximally and distally thereby actually pivoting the magazine about the pivot point.

The endoscopic section 14 is shown clearly in FIG. 14 and is mounted for rotation relative to the handle section 18. As noted above, the endoscopic section may be permanently attached to handle 12 as shown in a disposable instrument; alternatively as noted above, it may be removably attached to a re-usable handle, or a variety of other combinations or configurations.

The Endoscopic Section

Referring again to FIG. 14 the endoscopic section is shown in exploded view with parts separated for convenience of illustration and includes upper housing half section 14a and lower housing half section 14b. The housing half sections are preferably of a polycarbonate material such as LEXAN brand material mentioned previously, and are attached by welding, adhesives, etc. Positioned within the upper and lower housing half sections is pusher assembly 24 as described in more detail below, and anvil extension 88, formed of stainless steel and having a pair of elongated legs 90,92 which are joined at 94 at the distal end and which contain upwardly extending feet 88a,88b at the proximal end. As shown in FIG. 15, anvil extension 88 is attached at the distal end 94 to the staple storing magazine 16 by pivot pins 89 where the staple storing magazine is pivotally attached. The proximal connection points of anvil extension are best illustrated in FIG. 2 wherein upwardly bent feet 88a,88b are positioned within slots 15b in half round collar 15 which is fixedly attached to handle housing 12 by barrel 17 and nose piece 13 and related support members provided therein.

Anvil extension 88 is fabricated of stainless steel and its purpose is to stabilize the dimension of the endoscopic section 14 to prevent the forces acting on the components from stretching or compressing the upper and lower housing half sections 14a,14b of the endoscopic section which are constructed of a polycarbonate material such as LEXAN brand material. Thus, the steel anvil extension provides dimensional stability to the endoscopic section while the endoscopic section is supporting the components being subjected to forces for supporting, advancing and forming the surgical staples as will be described.

The Staple Firing System

Referring further to FIG. 14, the staple pusher assembly 24 is formed of firing rod 100 connected to flexible elongated firing wire 102 which is in turn connected to pusher plate assembly 104 as shown. The connection between firing rod 28 and firing wire 102 is a crimped or swaged connection at 106, whereas the connection between firing wire 102 and pusher 105 is accomplished by an interference fit between the firing wire 102 and collar 108 which is attached to pusher plate 104. Firing rod 28 and pusher plate 104 are preferably made of stainless steel whereas firing wire 102 is made to be resiliently flexible to accommodate the pivotal movement of the staple storing magazine 16 since firing wire 102 is located within the instrument at the location of staple magazine 16. In particular, firing wire 102 is preferably made of a super elastic metal. One example of such super elastic metal is NITINOL brand metal available from Raychem Corporation, Menlo Park, Calif. This material has a reduced tendency to fatigue after a substantial number of cycles of deflection caused by pivoting the staple storage magazine. Other resilient materials are also contemplated for firing wire 102.

The Staple Storage Magazine

Referring now to FIGS. 15 through 18, there is illustrated further details of the staple storing magazine 16. As noted previously, the staple storing magazine 16 is comprised of upper housing half 16a and lower housing half 16b suitably attached by welding,adhesives, etc. The magazine is adapted to contain a plurality of surgical staples 110 which are particularly shaped to penetrate and to attach surgical mesh to body tissue. For particular details of the shape of the staples constructed according to the invention, reference is made to FIG. 28.

Referring once again to FIGS. 15–18, a particular feature of the present invention resides in the system of storage of the staples 110 which are positioned in adjacent stacked relation whereby the stack of staples forms an angle with the longitudinal axis of the instrument of approximately 45 degrees as shown in FIG. 18. One purpose of stacking the staples as shown is to provide greater visibility to the user by the fact that the outer surface of the upper housing half section adjacent the stack of staples forms a similar angle and provides visibility to the user at the distal end of the staple storage magazine. Angular stacking of the staples as shown greatly facilitates storage of a plurality of staples in a structure configured and dimensioned for use in endoscopic applications, e.g., for use through a trocar guide tube of diameter of about 12 mm for example. The stack of staples 110 as shown in FIG. 18 is positioned and retained in such position by a resilient spring member 113 having dual resilient legs and whose side profile is curved as shown in FIG. 18.

The distal end of each leg engages the uppermost staple follower 114 in the form of a nylon insert having a general "H-shaped" configuration and dimensioned sufficient to cover the staples as best shown in FIG. 15. The nylon follower is intended to transmit the downward force of the staple retainer spring 113 so as to distribute the force on the stack of staples in a manner to facilitate a constant and uni-directional downward force on the lowermost staple which is positioned for advancement and deformation. It also functions to advance the stack of staples downwardly when the lowermost staple is fired. Steel anvil plate 120 is shown in FIG. 15 and includes upwardly extending feet 116 and 118 which form anvils at the distal end as shown in FIG. 15, for forming the staple therearound.

Thus, as seen in FIG. 18, the lowermost staple is identified by numeral 110L and is in a position for engagement by pusher plate 104 when the pusher assembly is advanced distally. The pusher plate 104 is shown clearly in FIGS. 15 and 18 and contains distally advancing lands 104R and 104L shown clearly in FIGS. 15 and 19 at the distal end to facilitate transmission of advancing force to the two rounded or arcuate bridge portions of the staple. This relative complementary configuration of the pusher plate 104 and the staple 110 facilitates efficient and uniform distribution of force to the staple when it is deformed about the anvil members as will be described.

The Staple Closing System

Referring now to FIGS. 17-24 there is illustrated the sequential views of the staple advancing and closing system between the pre-fired and fired condition of the staple. In particular, the staple and pusher mechanism are shown in FIG. 17 in the pre-fired condition while the staple shown in FIG. 24 is embedded within the body tissue in a manner to retain the surgical mesh to the body tissue.

In FIG. 17, the staple pusher assembly 24 is positioned proximal of the lowermost staple 110L and pusher plate 104 is correspondingly positioned proximal of the lowermost staple 110L. In FIGS. 18 and 19 the pusher plate 104 has been partially advanced distally and the lowermost staple 110L has been advanced distally of the stack of staples 110 in a manner such that the pusher plate 104 has now replaced lowermost staple 110L thereby preserving the integrity and position of the stack of staples 110. The preservation of the stack of staples 110 is provided by the fact that the thickness of the staple pusher plate 104 is either identical to or slightly less than the thickness of the staples to assume that the plate 104 will engage only one staple at a time.

Referring further to FIGS. 20 and 21 the pusher plate 104 has now advanced distally sufficient to cause the staple to penetrate the surgical mesh 112 and the body tissue 115. As shown in FIGS. 20 and 21, it can be seen that anvil members 116 and 118 are positioned for engagement by the straight sections of bridge portions 110BR and 110BL of the back rib of the staple 110L such that engagement of the staple by pusher plate 104 with the arcuate end corner portions of the staple as shown will cause the staple to deform in a predetermined manner as will be described.

In FIGS. 22-24 the staple 110L is now shown in the deformed condition about the anvil members 116 and 118 and the straight portions 110S of the back rib of the staple 110 are still in engagement with the anvils 116,118. In FIG. 22, the staple has penetrated into the body tissue 115 and has been deformed and in FIG. 24 the staple deformation is completed in a manner to substantially retain the surgical mesh 112 in attached position with respect to the body tissue as shown in FIG. 22. The inwardly projecting central portion or bight, 110C, of staple 110 is shown gripping the mesh and tissue in cooperation with the staple legs as shown in FIG. 24. However, release of-the staples from the anvil members 116,118 has not yet been completed.

Release of the staple from the anvil members 116,118 is readily accomplished by ejector spring 124 which is a "U-shaped" resilient spring having upwardly biased legs 124R and 124L each positioned respectively as shown in FIG. 15. When the pusher plate 104 is in the position shown in FIG. 20, the legs 124R and 124L of staple ejector spring are retained in a downward position by lands 104R and 104L of the pusher plate 104. However, when the pusher plate 104 is moved to the distalmost position shown in FIG. 23, the absence of the pusher plate permits staple ejector legs 124R and 124L to resiliently deflect upwardly to their natural configuration thereby creating a vertical separation between the anvil members 116,118 and the deformed staple, thus releasing the deformed staple from the anvil members as shown in FIG. 23. Continued proximal movement of the pusher plate 104 causes withdrawal of the pusher plate to a position entirely proximal of the stack of staples 110 as shown in FIG. 26, causing the stack of staples to move downwardly due to the downward force of resilient staple retainer spring 113 to advance the lowermost staple to the firing position.

Once the staple 110 is applied to the mesh 112 and tissue 115 as shown in FIGS. 22 and 24, the distal end of staple storing magazine 16 is withdrawn as shown in FIG. 24 and preparation is made for application of the next staple. FIG. 25 is a cross-sectional view taken along lines 25—25 of FIG. 24 with the staple storing magazine withdrawn from the surgical mesh and body tissue. Thereafter, the apparatus may be repositioned to apply another staple, or even an array of staples as shown in FIGS. 27 and 29.

Referring once again to FIG. 27, there is illustrated one form of surgical mesh repair of an opening in the body utilizing the apparatus and staple according to the invention. In the application shown in FIG. 27, a surgical mesh is attached to the body tissue over the opening as illustrated schematically at 115c in FIG. 27, and staples 110 have been applied in a circular array as shown to reinforce the repair. Beneath the mesh, the opening 115c may have previously been repaired as well. In FIG. 29 an alternative array of staples to apply mesh material to body tissue is shown. In this embodiment the mesh material 112 is essentially formed as a circular patch and staples 110 are oriented in a radial direction and are attached around the periphery of the patch such that one leg of the staple pierces the mesh and the other leg pierces body tissue 114. Essentially the staple bridges the periphery of the mesh material as shown. Clearly, alternative forms and arrangements are available to attach mesh or other surgery related objects or prostheses to body tissue as may come to the mind of persons skilled in the art.

It should be further noted that the repair of body tissue utilizing surgical mesh as shown in FIGS. 27 and 29 are exemplary, and that other applications of mesh and staples may be utilized in a manner to either reinforce a surgical repair or to encourage tissue growth. Such mesh materials are typically disclosed in U.S. Pat. Nos. 4,838,884, 4,665,221, 4,452,245, and 4,347,847. It is noted that the staple constructed according to the invention as shown in FIG. 28 is particularly adapted for attachment of such mesh material to body tissue according to any number of techniques which may readily come to the mind of those skilled in the art. In fact, in some instances the mesh may be formed as a plug for insertion into a surgical opening and then stapled. Moreover, the apparatus and staple of the present invention may be applied to attach other objects to body tissue as may come to the mind of those skilled in the art.

The Staple

Referring now once again to FIG. 28, there is illustrated the inventive staple 110 constructed according to the invention. The staple 110 is particularly shaped as shown, and is preferably formed of a length of wire of titanium. Stainless steel or equivalent material is also contemplated and the staple preferably has a rectangular cross-section as shown. Other cross-sections may be used. Typically, the wire will be about 0.38 mm in width (dimension w) and 0.51 mm in thickness (dimension T). The initial width of the staple before closure (dimension A) is about 4.4 mm and the-thickness dimension between the back rib and legs after closure (i.e. dimension B in FIG. 24) is about 3 mm. The staple 110 has a central bight portion 110C and a wire leg member 110R and 110L extending generally perpendicular to the central portion as shown. Each leg member 110R, 110L is connected to the central portion 110C by a bridge portion 110BR, 110BL having an arcuate corner portion as shown. Each leg member has a sharp tip for penetrating mesh and body tissue. Right leg member 110R further possesses a tapered surface 110TR at the tip which is opposite the position of the tapered surface 110TL at the tip of the other leg member 110L as shown in FIG. 28.

When the staple shown in FIG. 28 is advanced toward dual spaced anvils 116,118 as shown in FIG. 21 for example, and staple pusher plate 104 as shown, engages the arcuate portions of the bridge portions 110BR and 110BL, the legs of the staples are made to fold inwardly toward each other as shown for example in FIG. 22, with one leg crossing over the other. The cross-over configuration is automatically assumed by the legs because of the presence of tapered surfaces 110TR and 110TL which act as camming surfaces tending to bias each leg away from the other thereby tending to cross the legs in the manner shown. This structure also prevents interference of the legs when folded toward each other.

Thus, it can be seen that the particular shape of the staple as shown, promotes a unique folding pattern for the legs which achieves the configuration shown in the bent staples of FIGS. 22 and 24. Note in particular that inwardly bent central portion 110C promotes positive attachment of the mesh to the tissue by providing a gripping system between inwardly projecting bight portion 110C and leg members 110R and 110L with mesh and tissue gripped therebetween. This staple shape combines with the arrangement of the anvils and the particularly configured pusher plate 104 to cause the staple to pierce mesh and body tissue up to a predetermined extent. At this point, continued application of force to the staple causes the staple legs to fold upon themselves as shown in the drawings while encompassing a sufficient portion of the mesh to attach the mesh to the body tissue. Thus the staple pierces, folds and grips in substantially a single movement.

In practice, the laparoscopic procedures to repair tissue in hernia repair using surgical mesh is similar in some respects to the surgical procedures to gall bladders, appendix, lungs, etc. In particular, the endoscopic tubular section of the apparatus is inserted into the cannula which is positioned within the opening in the body. Provision is made between the cannula and the endoscopic section to seal the connection therebetween and provision may also be provided to seal the actual endoscopic apparatus from leakage of fluids or insufflating gaseous media. An exemplary cannula assembly including seal means is disclosed for example in commonly assigned U.S. Pat. No. 4,943,280, issued Jul. 24, 1990, the disclosure of which is incorporated herein by reference.

The Kit

The present invention is readily adaptable to be provided to surgeons in the form of a kit in which all necessary equipment and accessories are provided in sterile form ready for use in surgery. For example, an apparatus constructed according to the invention can be readily packaged with a supply of staples (i.e. up to 12 or more staples) and sufficient mesh material for completing the hernial repair. The mesh material is typically about 1 mm in thickness. The components may be provided separately as a matched kit, or in a blister type or other package, suitable and ready for use by the surgeon and the surgeon's assistants. The apparatus and staples can be provided in any size matched to meet the apparatus and mesh material in accordance with the particular needs of a contemplated hernial surgical procedure. In addition, the kit can include a matching trocar assembly with appropriate valve assembly to prevent loss of the insufflating gas from the peritoneum between the trocar and the outside surface of the endoscopic section. Since the outer housing of the endoscopic section is substantially closed at the point of attachment of the staple magazine, release of insufflating gases through the staple magazine and the endoscopic section housing is either non existent or minimal. Such trocar assembly is available from United States Surgical Corporation, Norwalk, Conn., under the trademark SURGIPORT brand trocar assembly.

A typical endoscopic section may be a 12 mm diameter with a staple magazine capable of holding up to 10 staples of appropriate size. The length of the endoscopic section is typically 14 to 15 inches. An endoscopic section in the embodiment shown will be about 14 inches. However, if pivotal movement of the staple storage magazine is to be provided between plus 45 degrees and minus 45 degrees solely by distal and proximal movement of collar 22, the endoscopic section will be structured to greater in length, i.e. about 15 inches. The trocar assembly will be of matching size, i.e., 12 mm, to accommodate the endoscopic section and to prevent release of gases thereby. The mesh material provided with the kit will be of mesh size comparable for use with the size of the staples provided in the kit.

Thus by structuring the apparatus to provide such sealing, the endoscopic application of staples to attach objects such as surgical mesh to body tissue can be readily accomplished. Accordingly, the present invention is not only directed to the apparatus for applying such staples to body tissue, but also to a kit in which the apparatus is uniquely combined with a supply of staples, surgical mesh, cannula assembly etc. whereby the surgeon may readily perform the necessary procedures.

What is claimed is:

1. A surgical staple formed from a continuous length of wire for attaching objects such as mesh materials to body tissue which comprises:

a) a central wire portion having a middle portion and first and second end portions, each said end portion extending at respective angles from said middle portion in a first direction;

b) first and second wire leg members extending generally perpendicular to said middle portion of said central wire portion, each said wire leg member having a free end portion for penetrating the object and body tissue when positioned in adjacent engaged relation therewith and advanced thereinto; and c) a bridge portion connecting each said first and second end portions to each said first and second wire leg members, respectively, each said bridge portion having a generally straight portion substantially parallel to said middle portion, each said bridge portion further having a first generally arcuate portion connected to each said straight portions and having a concave surface portion facing in a direction generally inwardly toward the opposing leg member, each said first generally arcuate portions connected to each said wire leg member and at least a portion of each said first generally arcuate portions extending from said straight portions and generally in said first direction, each said first and second wire leg members having a curved portion adjacent said bridge portion, each said curved portion being of generally concave configuration and facing in a direction generally opposite the direction of said first generally arcuate portion such that when each said bridge portion is supported against anvil member and force it is applied to said bridge portions on said wire leg members bend inwardly toward said central wire portion at respective locations inward of said first generally arcuate portions.

2. The surgical staple according to claim 1 wherein each said leg members has a pointed tip at said free end thereof to penetrate the object and the body tissue.

3. The surgical staple according to claim 2 wherein each said leg members has a tapered portion at said free end, said tapered portion on one leg member being located opposite said tapered portion on the other leg member such that when said leg members are folded inwardly toward each other each said tapered portion respectively cams the other leg member and the leg members are folded toward each other in adjacent relation without interference.

4. The surgical staple according to claim 3 wherein each said leg members has a generally arcuate shape having a concave portion thereof generally facing the other leg member.

5. The surgical staple according to claim 4 wherein said length of wire is made of titanium.

* * * * *